US010697014B2

(12) United States Patent
DeChow et al.

(10) Patent No.: US 10,697,014 B2
(45) Date of Patent: Jun. 30, 2020

(54) GENOMIC REGIONS WITH EPIGENETIC VARIATION THAT CONTRIBUTE TO PHENOTYPIC DIFFERENCES IN LIVESTOCK

(71) Applicant: The Penn State Research Foundation, University Park, PA (US)

(72) Inventors: Chad DeChow, Julian, PA (US); Wansheng Liu, State College, PA (US); Jurg W. Blum, Vettlingen (CH); Craig Baumrucker, State College, PA (US); Ti-Cheng Chang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 139 days.

(21) Appl. No.: 15/368,073

(22) Filed: Dec. 2, 2016

(65) Prior Publication Data

US 2017/0159121 A1 Jun. 8, 2017

Related U.S. Application Data

(60) Provisional application No. 62/262,460, filed on Dec. 3, 2015.

(51) Int. Cl.
*C12Q 1/68* (2018.01)
*C12P 19/34* (2006.01)
*C12Q 1/6876* (2018.01)

(52) U.S. Cl.
CPC ..... *C12Q 1/6876* (2013.01); *C12Q 2600/154* (2013.01)

(58) Field of Classification Search
CPC .. C12Q 1/6837; C12Q 1/6876; C12Q 1/6883; C12Q 2600/154
See application file for complete search history.

(56) References Cited

U.S. PATENT DOCUMENTS

| | | | |
|---|---|---|---|
| 5,614,364 | A | 3/1997 | Tuggle et al. |
| 2006/0037090 | A1 | 2/2006 | Andersson et al. |
| 2009/0305234 | A1 | 12/2009 | Olek et al. |
| 2010/0281547 | A1 | 11/2010 | Andersson et al. |
| 2011/0236905 | A1 | 9/2011 | Matsumoto et al. |
| 2013/0150465 | A1 | 6/2013 | Kragh et al. |
| 2014/0155296 | A1 | 6/2014 | Khatib et al. |

OTHER PUBLICATIONS

Wang, X.S. et al. Genet. Mol. Res. 12 (4): 6228-6239. (Year: 2013).*
Song F. et al., PNAS, vo. 102, No. 9, p. 3336-3341, Mar. 1 (Year: 2005).*
Dong, Y.C. et al. Acta Veterinaria et Zootechnica Sinica, vol. 46, No. 1, pp. 60-68—Abstract Only Provided (Year: 2015).*
Juppner, H. Bone vol. 17, No. 2, Supplement, 39S-42S, August (Year: 1995).*
Costello, J.F. et al. The Journal of Biological Chemistry, vol. 269, No. 25, Issue of Jun. 24, pp. 17228-17237, (Year: 1994).*
De Montera, B. et al, "Quantification of Leukocyte Genomic 5-Methylcytosine Levels Reveals Epigenetic Plasticity in Healthy Adult Cloned Cattle" Cellular Reprogramming vol. 12, No. 2, 2010 (Year: 2010).*
Furst, R.W. et al, "Is DNA methylation an epigenetic contribution to transcriptional regulation of the bovine endometrium during the estrous cycle and early pregnancy?", Molecular and Cellular Endocrinology 348 (2012) 67-77 (Year: 2012).*
Flisikowski et al., 2005, "Nucleotide sequence and variation of IGF2 gene exon 6 in Bos taurus and Bos indicus cattle", Anim Biotechnol 16(2):203-208.
Ogorevc et al., 2009, "Database of cattle candidate genes and genetic markers for milk production and mastitis", Animal Genetics 40: 832-851.
Stella et al., 2010, "Identification of Selection Signatures in Cattle Breeds Selected for Dairy Production", Genetics 185: 1451-1461.
Raven et al., 2014 "Multibreed genome wide association can improve precision of mapping causative variants underlying milk production in dairy cattle", BMC Genomics 15: 62: pp. 1-14.
Singh et al., 2012, "Epigenetics: a possible role in acute and transgenerational regulation of dairy cow milk production", Animal 6:3; pp. 375-381.
Gudex et al., 2014, "Prenatal Maternal and Possible Transgenerational Epigenetic Effects on Milk Production", PLoS One 9:e98928, pp. 1-6.
Abdel-Shafy et al., 2014, "Single nucleotide polymorphism and haplotype effects associated with somatic cell score in German Holstein cattle", Genet Sel Evol 46:35, pp. 1-10.
Ahrens et al., 2013, "DNA methylation analysis in nonalcoholic fatty liver disease suggests distinct disease-specific and remodeling signatures after bariatric surgery", Cell Metab 18(2):296-302.
Bethge et al., 2013, "Identification of highly methylated genes across various types of B-cell non-hodgkin lymphoma", PLoS One 8:e79602, pp. 1-10.
Brumbaugh et al., 2015, "Developmental origins of nonalcoholic fatty liver disease", Pediatr Res 75(0):140-147.
Cole et al., 2009, "Distribution and location of genetic effects for dairy traits", J Dairy Sci 92(6):2931-2946.
Daetwyler et al., 2014, "Whole-genome sequencing of 234 bulls facilitates mapping of monogenic and complex traits in cattle", Nat Genet 46(8):858-865.
Dechow et al., 2012, "The effect of sire selection on cow mortality and early lactation culling in adverse and favorable cow survival environments", Prev Vet Med 103(2-3):228-233.
Dechow et al., 2007, "Within-herd heritability estimated with daughter-parent regression for yield and somatic cell score", J Dairy Sci 90(1):482-492.
Erbe et al., 2012; "Improving accuracy of genomic predictions within and between dairy cattle breeds with imputed high-density single nucleotide polymorphism panels", J Dairy Sci 95:4114-4129.
Gelfman et al., 2013, When epigenetics meets alternative splicing: the roles of DNA methylation and GC architecture Epigenoics 5(4):351-353.

(Continued)

*Primary Examiner* — Stephen T Kapushoc
(74) *Attorney, Agent, or Firm* — Riverside Law LLP

(57) ABSTRACT

The invention provides compositions and methods for selecting milk-producing livestock with a preferred phenotype. In one embodiment, the method includes detecting methylation status of one or more genes and gene regulatory regions in a sample to identify the preferred phenotype.

1 Claim, 13 Drawing Sheets

(56) References Cited

OTHER PUBLICATIONS

Grisart et al., 2001, "Positional candidate cloning of a QTL in dairy cattle: identification of a missense mutation in the bovine DGAT1 gene with major effect on milk yield and composition", Genome Res 12(2):222-23.1.
Keating et al., 2015, "Epigenetics and metabolism.", Circ Res, 116(4):715-736.
Larson et al., 2006, "Discovery of eight novel divergent homologs expressed in cattle placenta", Physiol Genomics 25:405-413.
McConnel et al., 2010, "Conceptual modeling of postmortem evaluation findings to describe dairy cow deaths", J Dairy Sci 93(1):373-86.
Piccinato et al., 2010, "In vitro and in vivo analysis of fatty acid effects on metabolism of 17beta-estradiol and progesterone in dairy cows", J Dairy Sci 93(5):1934-43.
Riquet et al., 1999, "Fine-mapping of quantitative trait loci by identity by descent in outbred populations: Application to milk production in dairy cattle", PNAS 96:9252-7.
Schübeler, 2015, "Function and information content of DNA methylation", Nature 517:321-326.
VanRaden et al., 2009, "Invited review: reliability of genomic predictions for North American Holstein bulls", J Dairy Sci 92(1):16-24.
VanRaden et al., 2013, "Genomic imputation and evaluation using high-density Holstein genotypes", J Dairy Sci 96(1):668-78.

\* cited by examiner

GENOMIC REGIONS WITH EPIGENETIC VARIATION THAT CONTRIBUTE TO PHENOTYPIC DIFFERENCES IN LIVESTOCK

CROSS-REFERENCE TO RELATED APPLICATIONS

The present application is entitled to priority to U.S. Provisional Application No. 62/262,460, filed Dec. 3, 2015, which is incorporated by reference herein in its entirety.

STATEMENT REGARDING FEDERALLY SPONSORED RESEARCH OR DEVELOPMENT

This invention was made with government support under Contract No. 2008-34437-19335, and from Hatch Act Project No. PEN04266, awarded by The United States Department of Agriculture. The Government has certain rights in the invention.

BACKGROUND OF THE INVENTION

The production of milk by ungulate species facilitates the dairy and meat industries. This is most obvious for the production of dairy products, primarily through the Bovidae family; however, milk production also facilitates growth in other production animals, such as swine, where increased milk production results in more efficient growth of offspring.

The effects of genetic selection for milk yield in dairy cattle have been well documented beginning in the 1960s (https://www.cdcb.us/eval/summary/trend.cfm). For example, Holstein cattle have increased in genetic merit for milk production by 8183 pounds annually, a ~59% increase. Changes to cow housing, feeding, and management have increased milk yield by an additional 5517 pounds, with the combined effect of genetic selection and management resulting in an approximate doubling of milk yield in five decades. Most species have less organized genetic selection programs than dairy cattle.

Nevertheless, milk yield in goats was reported to increase from 1 to 20 pounds per year, depending on breed, due to genetic selection (http://aipl.arsusda.gov/reference/goat/goatsfs.html).

The effect of improved genetic potential for milk yield can also be demonstrated in non-dairy animals. Genetic selection in Angus beef cattle has increased calf weaning weight by 56 pounds since 1980 (http://www.angus.org/Nce/GeneticTrends.aspx); of that, it is estimated that 24 pounds are due to higher milk production by calves' mothers. In Yorkshire swine, the weight of a typical sow's litter by 21-days has increased by 13 pounds which requires a large increase in milk production (https://mail.nationalswine.com:8443/newstages/TraitLeaderReports.aspx).

While highly successful, the genes and physiological processes which have been altered to facilitate such increases remain elusive. A notable exception is a binucleotide substitution in the DGAT1 gene of dairy cattle that causes a lysine to alanine substitution at position 232 (K232A) (Riquet et al., 1999; Grisart et al., 2002). The alanine variant results in higher milk and protein yields, but is not economically advantageous in many markets because of a substantial correlated decline in milk-fat yield. Mutations in the same gene also influences milk-fat production of buffalo (*Bubalus bubalis*) (Cardoso et al., 2015), may alter meat quality in swine (Li et al., 2013), and carcass characteristics in beef cattle (Tait et al., 2014). Much genetic research has focused on the identification of QTL (quantitative trait loci), such as DGAT1, with strong influences on performance. However, there has been little effort expended toward identifying epigenetic-QTL. One theory is that genetic selection may act partly through altered epigenetic profiles as DNA sequence variation is reported to cause shifts in DNA methylation (Schübeler, 2015).

More recently, animal industries have incorporated genotyping of single nucleotide polymorphisms (SNP) into genetic selection programs (http://www.illumina.com/products/by-type/microarray-kits.html). Genomic predictions of genetic merit for a variety of traits are facilitated by marker genotypes for thousands of loci spread across the genome (VanRaden et al., 2009). Genomic analysis has largely confirmed the quantitative model of many small effects that cumulatively result in a high degree of variation (Cole et al., 2009), but understanding of how selection alters performance remains elusive.

It is clear that genetic selection has been successful in improving animal performance, but there are many animals for which their estimates of genetic merit fail to correspond to actual phenotypic performance. This has been largely attributed to "preferential treatment" by many authors (Bolgiano et al., 1979; Kuhn et al., 1994; Powell et al., 1994; Weigel et al., 1994; Kuhn and Freeman, 1995; Kuhn et al., 1999). Preferential treatment occurs when an animal is provided with an advantageous environment, a higher plane of nutrition for instance, compared with its contemporaries. The estimate of an animal's genetic merit is thought to then be inflated because of the effect of preferential treatment rather than a true genetic difference. Recently, adjustments were made to deflate genetic evaluations from elite cows in an effort to reduce potential bias from preferential treatment (Wiggans et al., 2011).

While preferential treatment of more valuable animals could bias genetic evaluation to some degree, farmers have economic incentive to maximize performance from all animals and not a selected few. This makes widespread preferential treatment less likely and calls for alternative explanations of mismatches between genetic predictions of performance and actual performance.

There is strong evidence that mechanisms other than preferential treatment deviate performance from expectations based on traditional genetic evaluations. It was previously demonstrated that heritability estimated through female lineages is higher than that estimated through male lineages (Dechow and Norman, 2007); this implies that there are inherited maternal genetic effects that are not fully captured by the additive genetic relationship model that underlies current genetic and genomic evaluation systems. Such effects are also apparent in crossbreeding studies and are often attributed to "cytoplasmic" or "mitochondrial" effects (Schutz et al., 1992; McAllister, 2002). A strong maternal influence independent of variation arising from DNA sequence differences among animals would create that appearance of inflated female genetic evaluations.

Epigenetic modifications may be the molecular mechanism that underlies much of what is perceived as "preferential treatment", "cytoplasmic", or "mitochondrial effects". The effects of DNA methylation on the performance of animal clones (Akagi et al., 2013) has long been recognized, and papers have speculated that epigenetic modifications could alter animal performance (Roche et al., 2009; Couldrey and Cave, 2014). While SNP based genotyping chips are available for many members of Bovidae and ungulate species, DNA methylation chips are not available even though such technology has been developed for humans.

Similarly, a pubmed search for QTL identifies matches for many ungulates including cattle, swine, buffalo, goats, sheep, and horse. However, a search for epiallele or epigenetic-QTL provides no results for these species; they are provided by human and plant searches. No sites of differential methylation associated with high or low milk yield have been identified to date.

Differential methylation associated with other important phenotypic characteristics have also not been identified. Of particular interest would be linkages between epigenetic variation and the health of cows. Selection for higher production (Shook, 1989), fertility (VanRaden et al., 2004), and modern management practices (Dechow et al., 2011) have been shown to degrade animal health and wellbeing.

There is a need in the art for a method capable of identifying animals with high performance that cannot otherwise be identified with current genetic and genotyping methods alone. The present invention addresses this unmet need. There is a need in the art for a method capable of identifying dairy cows and other dairy-producing livestock with high milk, fat and protein yields that cannot otherwise be identified with genetics alone. The present invention addresses this unmet need.

SUMMARY OF THE INVENTION

The present invention relates to compositions and methods for selecting milk-producing livestock with a preferred phenotype using a biological sample collected from the livestock. In one embodiment, the invention provides a method of selecting a livestock with a preferred phenotype. In one embodiment, the method comprises determining the level of methylation of a biomarker in a biological sample of the livestock, comparing the level of methylation of the biomarker in the sample of the livestock with a comparator control, and selecting the livestock based on whether the level of methylation of the biomarker is higher or lower than the level of methylation of the comparator control.

In one embodiment, the method is used to determine the level of methylation of a biomarker in a biological sample of the livestock. In one embodiment, the biological sample includes leukocytes. In one embodiment, the method relates to comparing the level of methylation of the biomarker in the sample of the livestock with a comparator control. In one embodiment, the method comprises selecting the livestock based on whether the level of methylation of the biomarker is higher or lower than the level of methylation of the comparator control.

In one embodiment, the method relates to detecting a differentially methylated genomic region (DMR). In one embodiment, the method comprises selecting a DMR from one or more DMR set forth in the included Table 2. In one embodiment, the method comprises selecting a DMR from the group consisting of DMR377, DMR386, DMR350, and any combination thereof.

In one embodiment, the method comprises selecting livestock when the level of methylation of a DMR is lower than the methylation of the DMR of a control animal.

In one embodiment, the method comprises selecting a DMR from the following group: DMR233, DMR352, DMR378, DMR379, DMR367, DMR383, and any combination thereof.

In one embodiment, the method comprises selecting livestock when the level of methylation of a DMR is higher than the methylation of the DMR of a control animal.

In one embodiment, the method comprises measuring the level of the biomarker by detecting the methylation of CpG sequences in the promoter, gene or related regulatory sequence of the biomarker. In one embodiment, the CpG sequences are located on promoter sequences upstream of coding sequences, in the coding regions, in enhancer regions, in intron regions, and any combination thereof.

In one embodiment, the method comprises measuring the level of methylation of the biomarker using PCR, methylation-specific PCR, real-time methylation-specific PCR, PCR assay using a methylation DNA-specific binding protein, quantitative PCR, a DNA chip-based assay, pyrosequencing, bisulfate pyrosequencing, and Methylated DNA immunoprecipitation-sequencing.

In one embodiment, the control animal is used to determine the level of the biomarker in the sample of a normal livestock. In one embodiment, the comparator control is a positive control, a negative control, a historical control, or a historical norm.

In one embodiment, the method of the present invention comprises livestock that is a cow, buffalo, bison, goat, sheep, camel, donkey, horse, pigs, reindeer, moose and yak. In one embodiment, the livestock is a *Bos taurus* cattle.

In one embodiment, the preferred phenotype is high milk-yielding, high fat-yielding, high protein-yielding, and any combination thereof.

In one embodiment, the present invention provides a kit for selecting a livestock, wherein the kit contains a reagent for measuring the level of methylation of a biomarker in a biological sample of the livestock wherein the biomarker is a differentially methylated genomic region (DMR). In one embodiment, the kit selects a DMR from one or more genomic regions set forth in Table 2. In one embodiment, the DMR is selected from the following group: DMR377, DMR386, DMR233, DMR352, DMR378, DMR379, DMR367, DMR383, and any combination thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts Alignments for MYOM2. FIG. 1B demonstrates alignments for PNMT. FIG. 1C depicts the MYOM2 reads per nucleotide represented with blue lines and geometric means represented with red lines. FIG. 1D depicts the PNMT reads per nucleotide represented with blue lines and geometric means represented with red lines.

FIG. 6, comprising FIG. 6A depicts the 1 Mb region of chromosome 20 where DMR 386 is located. FIG. 6B depicts the average number of mapped reads for high cows and their controls for DMR 386 which is 1692 bp upstream of a gene on the positive DNA strand FIG. 7, comprising FIG. 7A depicts the 1 Mb region of chromosome 18 where DMR 352 is located. FIG. 7B depicts number of mapped reads for high cows and their controls for DMR 352 which is 92 bp upstream of a gene on the negative DNA strand.

FIG. 8, comprising FIG. 8A depicts the 1 Mb region of chromosome 10 where DMR 233 is located. FIG. 8B depicts the average number of mapped reads for high cows and their controls for a DMR with no nearby annotated features.

FIG. 9, comprising FIG. 9A depicts the 1 Mb region of chromosome 19 where DMR 378 and 379 are located. FIG. 9B depicts the average number of mapped reads for high cows and their controls for two DMR that are in close proximity to each other in SECTM1 region of BTA 19.

FIG. 10, comprising FIG. 10A depicts the 1 Mb region of chromosome 19 where DMR 377 is located. FIG. 10B depicts the average number of mapped reads for high cows and their controls for a DMR in the proximity of the KRT family of genes, including 3146 bp downstream of KRT14 which is on the negative strand.

FIG. 11, comprising FIG. 11A depicts the 1 Mb region of chromosome 19 where DMR 367 is located. FIG. 11B depicts the average number of mapped reads for high cows and their controls for a DMR that is located within a gene intron.

FIG. 12, comprising FIG. 12A depicts the 1 Mb region of chromosome 20 where DMR 383 is located. FIG. 12B depicts the average number of mapped reads for high cows and their controls for a DMR that is located within two protein-coding genes.

DETAILED DESCRIPTION

Figure 1A:
FIG. 1A through FIG. 1D, is a series of images showing the Alignments (Integrative Genomics Viewer; Robinson et al., 2011; Thorvaldsdóttir et al., 2012), reads per nucleotide, and geometric means reads for all eight cows from 400 bp upstream to 50 bp downstream of the transcription start site (TSS) of MYOM2 and PNMT.

The present invention is based on the discovery that regions of differential methylation were evident when comparing milk-producing livestock such as cows buffalo, bison, goat, sheep, camel, donkey, horse, pigs, reindeer, moose and yak, with extreme high milk, fat and protein yields to control cows and other milk-producing livestock such as cows, buffalo, bison, goat, sheep, camel, donkey, horse, pigs, reindeer, moose and yak from the same farm.

The present invention relates to compositions and methods for selecting cattle and other milk-producing livestock with preferred phenotypic differences, including but not limited to, selection of livestock with increased milk, fat, and protein production. In particular, the present invention relates to methylation levels of DNA as biomarkers and for livestock selection.

Accordingly, embodiments of the present invention provide compositions, kits, and methods useful in the selection of livestock. Experiments conducted during the course of development of embodiments of the present invention identified differential methylated regions in livestock producing high milk yield livestock as compared to control livestock as well as 1463 genes located in significant partially methylated domains (PMD) in which the odds of gene expression for genes not in a PMD compared to those within a PMD was 1.66:1. Some embodiments of the present invention provide compositions and methods for detecting such methylated DNA. Identification of differential DNA methylation is useful in selection, screening, diagnostic and research uses.

In some embodiments, methylation is altered in one or more of the described biomarker in livestock with a preferred phenotype. For example, in some embodiments, methylation of biomarkers is increased relative to a control sample from a subject that does not have the preferred phenotype (e.g., a population average of samples, a control sample, etc.). In other embodiments, methylation of biomarkers is decreased relative to a control sample from a subject that does not have the preferred phenotype (e.g., a population average of samples, a control sample, etc.). Accordingly, the invention in some instances provides a combination of markers for the preferred phenotype, wherein some of the markers include decreased methylation of a biomarker and other markers include increased methylation of a biomarker.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±40% or ±20% or ±10%, ±5%, ±1%, or ±0.1% from the specified value, as such variations are appropriate.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type, might be abnormal for a different cell or tissue type.

The terms "biomarker" and "marker" are used herein interchangeably. They refer to a substance that is a distinctive indicator of a biological process, biological event, biological phenotype and/or pathologic condition.

The phrase "body sample" or "biological sample" is used herein in its broadest sense. A sample may be of any biological tissue or fluid from which biomarkers of the present invention may be assayed. Examples of such samples include but are not limited to blood, saliva, buccal smear, feces, lymph, urine, gynecological fluids, biopsies, amniotic fluid and smears. Samples that are liquid in nature are referred to herein as "bodily fluids." Body samples may be obtained from a subject by a variety of techniques including, for example, by scraping or swabbing an area or by using a needle to aspirate bodily fluids. Methods for collecting various body samples are well known in the art. Frequently, a sample will be a "clinical sample," i.e., a sample derived from a subject. Such samples include, but are not limited to, bodily fluids which may or may not contain cells, e.g., blood (e.g., whole blood, serum or plasma), urine, saliva, tissue or fine needle biopsy samples, and archival samples with known diagnosis, treatment and/or outcome history. Biological or body samples may also include sections of tissues such as frozen sections taken for histological purposes. The sample also encompasses any material derived by processing a biological or body sample. Derived materials include, but are not limited to, cells (or their progeny) isolated from the sample, proteins or nucleic acid molecules extracted from the sample. Processing of a biological or body sample may involve one or more of: filtration, distillation, extraction, concentration, inactivation of interfering components, addition of reagents, and the like.

In the context of the present invention, the term "control," when used to characterize a subject, refers, by way of non-limiting examples, to a subject that is healthy, to a subject not having the preferred phenotype. The term "control sample" refers to one, or more than one, sample that has been obtained from a healthy subject or from a tissue from a subject not having the preferred phenotype.

The term "control or reference standard" describes a material comprising none, or a normal, low, or high level of one of more of the marker (or biomarker) expression products of one or more of the markers (or biomarkers) of the invention, such that the control or reference standard may serve as a comparator against which a sample can be compared.

The term "CpG island" refers to a contiguous region of genomic DNA that satisfies the criteria of a "GC Content">0.5. CpG islands are typically, but not always, between about 0.2 to about 1 kb, or to about 2 kb in length.

"Differentially increased levels" refers to biomarker methylation levels including which are at least 1%, 2%, 3%, 4%, 5%, 10% or more, for example, 5%, 10%, 20%, 30%, 40%, or 50%, 60%, 70%, 80%, 90% higher or more, and/or 0.5 fold, 1.1 fold, 1.2 fold, 1.4 fold, 1.6 fold, 1.8 fold higher or more, as compared with a control.

"Differentially decreased levels" refers to biomarker methylation levels which are at least at least 1%, 2%, 3%, 4%, 5%, 10% or more, for example, 5%, 10%, 20%, 30%, 40%, or 50%, 60%, 70%, 80%, 90% lower or less, and/or 0.9 fold, 0.8 fold, 0.6 fold, 0.4 fold, 0.2 fold, 0.1 fold or less, as compared with a control.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease, or disorder, the frequency with which such a sign or symptom is experienced by a patient, or both, is reduced.

As used herein "endogenous" refers to any material from or produced inside the organism, cell, tissue or system.

"Epigenetic parameters" are, in particular, cytosine methylation. Further epigenetic parameters include, for example, the acetylation of histones which, however, cannot be directly analysed using the described method but which, in turn, correlate with the DNA methylation. As used herein, the term "exogenous" refers to any material introduced from or produced outside the organism, cell, tissue or system. The term "expression" as used herein is defined as the transcription and/or translation of a particular nucleotide sequence driven by its promoter.

The term "hypermethylation" refers to the average methylation state corresponding to an increased presence methylated nucleotides. In some embodiments, the hypermethylation corresponds to an increase of 5-mCyt at one or a plurality of CpG dinucleotides or within a DNA sequence of a test DNA sample, relative to the amount of 5-mCyt found at corresponding CpG dinucleotides within a normal control DNA sample.

The term "hypomethylation" refers to the average methylation state corresponding to a decreased presence methylated nucleotides. In some embodiments, the hypomethylation corresponds to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

The "level" of one or more biomarkers means the absolute or relative amount or concentration of the biomarker in the sample. The term "level" also refers to the absolute or relative amount of methylation of the biomarker in the sample.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

The term "Methylation assay" refers to any assay for determining the methylation state of one or more CpG dinucleotide sequences within a sequence of DNA.

The term "methylation state" or "methylation status" refers to the presence or absence of 5-methylcytosine ("5-mCyt") at one or a plurality of CpG dinucleotides within a DNA sequence. Methylation states at one or more particular CpG methylation sites (each having two antiparallel CpG dinucleotide sequences) within a DNA sequence include "unmethylated," "fully-methylated" and "hemimethylated."

The terms "methylation-specific restriction enzymes" or "methylation-sensitive restriction enzymes" shall be taken to mean an enzyme that selectively digests a nucleic acid dependant on the methylation state of its recognition site. In the case of such restriction enzymes which specifically cut if the recognition site is not methylated or hemimethylated, the cut will not take place, or with a significantly reduced efficiency, if the recognition site is methylated. In the case of such restriction enzymes which specifically cut if the recognition site is methylated, the cut will not take place, or with a significantly reduced efficiency if the recognition site is not methylated. Preferred are methylation-specific restriction enzymes, the recognition sequence of which contains a CG dinucleotide (for instance cgcg or cccggg). Further preferred for some embodiments are restriction enzymes that do not cut if the cytosine in this dinucleotide is methylated at the carbon atom C5.

"Non-methylation-specific restriction enzymes" or "non-methylation-sensitive restriction enzymes" are restriction enzymes that cut a nucleic acid sequence irrespective of the methylation state with nearly identical efficiency. They are also called "methylation-unspecific restriction enzymes."

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand that are located 5' to a reference point on the DNA are referred to as "upstream sequences"; sequences on the DNA strand which are 3' to a reference point on the DNA are referred to as "downstream sequences."

As used herein, "predisposition" refers to the property of being susceptible to a cellular proliferative disorder. A subject having a predisposition to a cellular proliferative disorder has no cellular proliferative disorder, but is a subject having an increased likelihood of having a cellular proliferative disorder.

A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

A "reference level" of a biomarker means a level of the biomarker, for example level of methylation of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype.

By the term "specifically binds," as used herein, is meant a molecule, such as an antibody, which recognizes and binds to another molecule or feature, but does not substantially recognize or bind other molecules or features in a sample.

"Standard control value" as used herein refers to a predetermined methylation level of a biomarker. The standard control value is suitable for the use of a method of the present invention, in order for comparing the amount of methylation of a biomarker of interest that is present in a sample. An established sample serving as a standard control provides an average amount methylation of a biomarker of interest that is typical for an average, healthy subject of reasonably matched background. A standard control value may vary depending on the biomarker of interest and the nature of the sample.

As used herein, the term "subject" refers to a human or another mammal (e.g., cow, primate, dog, cat, goat, horse, pig, mouse, rat, rabbit, and the like). In many embodiments of the present invention, the subject is a cow. In such embodiments, the subject is often referred to as an "individual" or a "patient." The terms "individual" and "patient" do not denote a particular age.

As used herein, the term "livestock" refers to a mammal, used for the purpose of producing milk (eg., cow, buffalo, bison, goat, sheep, camel, donkey, horse, pig, reindeer, moose, yak, and the like) or where milk production facilitates offspring growth for the purposes of meat production.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based partly on the discovery of 500 differentially methylated DNA regions (DMR) between high milk yield cows and their control. Examples of significant DMR include regions corresponding to an 830 bp region on BTA10 (DMR233) which was >500 kb away from annotated genes, locations on BTA17 corresponding to the gene HORMAD2 (DMR350), and locations on BTA19 corresponding to genes SECTM1A, LOC781977, LOC10033649, LOC100300790, CD7, and non-coding RNA LOC10190343 (DMR378, DMR379). The high-milk yield cows had higher levels of methylation than control livestock on the DMR in BTA19 but lower levels of DNA methylation on the DMR in BTA17.

The invention is also based on the identification of partially methylated domains (PMD) and the identity of 1463 genes located within PMD. Comparison of expression of genes located within PMD to non-PMD genes revealed that the odds of expression for genes not in a PMD compared with those within a PMD were 1.66:1, which was highly significant. After functional evaluation, six significant functional annotations were found: olfactory receptor activity, olfactory transduction, G-protein coupled receptor (GPCR) protein signaling pathway, cell surface receptor linked signal transduction, intrinsic to membrane, and integral to membrane.

Accordingly, the invention provides biomarkers for phenotypic variation when selecting livestock. In one embodiment, the biomarker is differentially methylated and can be effectively used for the selection of livestock with a preferred phenotype.

In one embodiment the livestock include, but are not limited to, cow, buffalo, goat, sheep, camel, donkey, horse, pigs, reindeer and yak.

In one embodiment, the biomarkers of the invention include a differentially methylated region (DMR) selected from one or more in table 2.

In one embodiment, the DMR includes, but is not limited to, DMR377, DMR386, DMR233, DMR352, DMR378, DMR379, DMR367, DMR383, DMR350, DMR384, and any combination thereof.

In one embodiment, biomarkers of the invention include one or more of SECTM1A, LOC781977, LOC10033649, LOC100300790, and CD7. In one embodiment, biomarkers of the invention include one or more of DMR378 and DMR379. In one other embodiment, the present invention includes a method for detecting the methylation of HORMAD2, or DMR350 and a kit for determining a course of treatment using the same.

In one embodiment, detection of an increased level of a biomarker is used to identify the preferred phenotype wherein the biomarker includes, but is not limited to, DMR233, DMR352, DMR378, DMR379, DMR367, DMR383, and any combination thereof.

In one embodiment, detection of an increased level of methylation of a biomarker, wherein the biomarker is selected from the group consisting of SECTM1A, LOC781977, LOC10033649, LOC100300790, and CD7, DMR378 and DMR379 and any combination thereof, is used to identify the preferred phenotype.

In one embodiment, detection of a decreased level of a biomarker is used to identify the preferred phenotype wherein the biomarker includes, but is not limited to, DMR386, DMR377, DMR350 and any combination thereof.

In another embodiment, detection of a decreased level of methylation of a biomarker, wherein the biomarker is HORMAD2, is used to identify the preferred phenotype.

In yet another embodiment, detection of a decreased level of methylation of a biomarker, wherein the biomarker is DMR350, is used to identify the preferred phenotype.

Additional aspects provide novel methods and compositions for determining the relationship between methylation status and other variables including, but not limited to age, family history, and single nucleotide polymorphisms.

Biomarkers

The present invention provides DNA methylation markers associated preferred phenotypes when selecting livestock. Accordingly, a DNA methylation marker associated with phenotypic variation is considered a biomarker in the context of the present invention.

A biomarker is an organic biomolecule which is differentially present in a sample taken from an individual of one phenotypic status (e.g., having a disease) as compared with an individual of another phenotypic status (e.g., not having the disease). A biomarker is differentially present between the two individuals if the mean or median expression level, including methylation level, of the biomarker in the different individuals is calculated to be statistically significant. Biomarkers, alone or in combination, provide measures of relative risk that an individual belongs to one phenotypic status or another. Therefore, they are useful as markers for diagnosis of disease, the severity of disease, therapeutic effectiveness of a drug, and drug toxicity.

Accordingly, the invention provides methods for identifying one or more biomarkers that can be used to prediction of and selection based on phenotypic outcomes. The methods of the invention are carried out by obtaining a set of measured values for a plurality of biomarkers from a biological sample derived from a test individual, obtaining a set of measured values for a plurality of biomarkers from a biological sample derived from a control individual, comparing the measured values for each biomarker between the test and control sample, and identifying biomarkers which are significantly different between the test value and the control value, also referred to as a reference value.

The process of comparing a measured value and a reference value can be carried out in any convenient manner appropriate to the type of measured value and reference value for the biomarker of the invention. For example, "measuring" can be performed using quantitative or qualitative measurement techniques, and the mode of comparing a measured value and a reference value can vary depending on the measurement technology employed. For example, when a qualitative colorimetric assay is used to measure biomarker levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the invention will most commonly be quantitative values (e.g., quantitative measurements of concentration). In other examples, measured values are qualitative. As with qualitative measurements, the comparison can be made by inspecting the numerical data, or by inspecting representations of the data (e.g., inspecting graphical representations such as bar or line graphs).

A measured value is generally considered to be substantially equal to or greater than a reference value if it is at least about 95% of the value of the reference value. A measured value is considered less than a reference value if the measured value is less than about 95% of the reference value. A measured value is considered more than a reference value if the measured value is at least more than about 5% greater than the reference value.

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for a desired biomarker. Alternately, a separate device (e.g., a digital computer) may be used to compare the measured value(s) and the reference value(s). Automated devices for comparison may include stored reference values for the biomarker(s) being measured, or they may compare the measured value(s) with reference values that are derived from contemporaneously measured reference samples.

Methylation

In the present invention, any nucleic acid sample, in purified or nonpurified form, can be used, provided it contains or is suspected of containing a nucleic acid sequence containing a target locus (e.g., CpG-containing nucleic acid). One nucleic acid region capable of being differentially methylated is a CpG island, a sequence of nucleic acid with an increased density relative to other nucleic acid regions of the dinucleotide CpG. The CpG doublet occurs in vertebrate DNA at only about 20% of the frequency that would be expected from the proportion of G*C base pairs. In certain regions, the density of CpG doublets reaches the predicted value; it is increased by ten-fold relative to the rest of the genome. CpG islands have an average G*C content of about 60%, compared with the 40% average in bulk DNA. The islands take the form of stretches of DNA typically about one to two kilobases long. There are about 45,000 islands in the human genome.

In many genes, the CpG islands begin just upstream of a promoter and extend downstream into the transcribed region. Methylation of a CpG island at a promoter usually suppresses expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g., exons), downstream of coding regions in, for example, enhancer regions, and in introns. Differential methylation can also occur outside of CpG islands.

Typically, the CpG-containing nucleic acid is DNA. However, the inventive method may employ, for example, samples that contain DNA, or DNA and RNA containing mRNA, wherein DNA or RNA may be single-stranded or double-stranded, or a DNA-RNA hybrid may be included in the sample.

A mixture of nucleic acids may also be used. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. Nucleic acids contained in a sample used for detection of methylated CpG islands may be extracted by a variety of techniques such as that described elsewhere herein or procedures known to those of skill in the art.

Nucleic acids isolated from a subject are obtained in a biological sample from the subject. Such samples may be obtained by various medical procedures known to those of skill in the art.

In one aspect of the invention, the state of methylation in nucleic acids of the sample obtained from a subject is hypermethylation compared with the same regions of the nucleic acid in a subject not having the preferred phenotype. Hypermethylation as used herein refers to the presence or an increase of methylation in one or more nucleic acids. Nucleic acids from a subject not having the preferred phenotype contain no detectable or lower levels of methylated biomarkers when the same nucleic acids are examined.

In another aspect of the invention, the state of methylation in nucleic acids of the sample obtained from a subject are hypomethylated. Hypomethylation as used herein refers to the absence or diminished level of methylated biomarkers in one or more nucleic acids. Nucleic acids from a subject not having the preferred phenotype contain detectable or higher levels of methylated alleles when the same nucleic acids are examined.

Accordingly, the invention in some instances provides a combination of markers for a preferred phenotype, wherein some of the markers include decreased methylation of a gene and other markers include increased methylation of a gene.

Detection Methods

In one embodiment, the invention provides diagnostic and screening methods that utilize the detection of aberrant methylation of genes, promoters, or gene regulatory regions such as the differentially methylated regions listed in table 2 (e.g., including, but not limited to, DMR377, DMR386, DMR233, DMR352, DMR378, DMR379, DMR367, DMR383, DMR350, DMR384, HORMAD2, SECTM1A, LOC781977, LOC10033649, LOC100300790, CD7, and LOC10190343). In some embodiments, methylation of a gene is altered (e.g., increased or decreased). That is, in one embodiment, methylation of a gene is decreased relative to a control sample from a subject that does not have the preferred phenotype (e.g., a population average of samples, a control sample, etc.). In another embodiment, methylation of a gene is increased relative to a control sample from a subject that does not have the preferred phenotype (e.g., a population average of samples, a control sample, etc.). Accordingly, the invention in some instances provides a combination of markers for phenotypic variation, wherein some of the markers include decreased methylation of a gene and other markers include increased methylation of a gene.

Any patient sample suspected of containing the aberrantly methylated genes or promoters may be tested according to methods of embodiments of the present invention. In some embodiments, the patient sample is subjected to preliminary processing designed to isolate or enrich the sample for the aberrantly methylated genes or promoters or cells that contain the aberrantly methylated genes or promoters. A variety of techniques known to those of ordinary skill in the art may be used for this purpose, including but not limited to: centrifugation; immunocapture; cell lysis; and, nucleic acid target capture.

In one embodiment, the biomarkers of the invention can be detected using a real-time methylation specific PCR procedure. Real-time methylation-specific PCR is a real-time measurement method modified from the methylation-specific PCR method and comprises treating genomic DNA with bisulfite, designing PCR primers corresponding to the methylated base sequence, and performing real-time PCR using the primers. Methods of detecting the methylation of the genomic DNA include two methods: a method of detection using, for example, a TaqMan™ probe complementary to the amplified base sequence; and a method of detection using Sybergreen™. Thus, the real-time methylation-specific PCR allows selective quantitative analysis of methylated DNA. A standard curve is plotted using an in vitro methylated DNA sample, and a gene containing no 5'-CpG-3' sequence in the base sequence is also amplified as a negative control group for standardization to quantitatively analyze the degree of methylation.

In one embodiment, the biomarkers of the invention can be detected using a pyrosequencing procedure. The pyrosequencing method is a quantitative real-time sequencing method modified from the bisulfite sequencing method. Similarly to bisulfite sequencing, genomic DNA is converted by bisulfite treatment, and then, PCR primers corresponding to a region containing no 5'-CpG-3' base sequence are constructed. Specifically, the genomic DNA is treated with bisulfite, amplified using the PCR primers, and then subjected to real-time base sequence analysis using a sequencing primer. The degree of methylation is expressed as a methylation index by analyzing the amounts of cytosine and thymine in the 5'-CpG-3' region.

In one embodiment, the biomarkers of the invention can be detected via a PCR using a methylation-specific binding protein or a DNA chip. PCR using a methylation-specific binding protein or a DNA chip assay allows selective isolation of only methylated DNA. Genomic DNA is mixed with a methylation-specific binding protein, and then only methylated DNA was selectively isolated. The isolated DNA is amplified using PCR primers corresponding to the promoter region, and then methylation of the DNA is measured by agarose gel electrophoresis.

In addition, methylation of DNA can also be measured by a quantitative PCR method, and methylated DNA isolated with a methylated DNA-specific binding protein can be labeled with a fluorescent probe and hybridized to a DNA chip containing complementary probes, thereby measuring methylation of the DNA.

In one embodiment, the biomarkers of the invention can be detected by way of using a methylation-sensitive restriction endonuclease. Detection of differential methylation can be accomplished by bringing a nucleic acid sample into contact with a methylation-sensitive restriction endonuclease that cleaves only unmethylated CpG sites. In a separate reaction, the sample is further brought into contact with an isoschizomer of the methylation-sensitive restriction enzyme that cleaves both methylated and unmethylated CpG-sites, thereby cleaving the methylated nucleic acid.

Methylation-sensitive restriction endonucleases can be used to detect methylated CpG dinucleotide motifs. Such endonucleases may either preferentially cleave methylated recognition sites relative to non-methylated recognition sites or preferentially cleave non-methylated relative to methylated recognition sites. Examples of the former are Acc III, Ban I, BstN I, Msp I, and Xma I. Examples of the latter are Acc II, Ava I, BssH II, BstU I, Hpa II, and Not I. Alternatively, chemical reagents can be used which selectively modify either the methylated or non-methylated form of CpG dinucleotide motifs.

Specific primers are added to the nucleic acid sample, and the nucleic acid is amplified by any conventional method. The presence of an amplified product in the sample treated with the methylation-sensitive restriction enzyme but absence of an amplified product in the sample treated with the isoschizomer of the methylation-sensitive restriction enzyme indicates that methylation has occurred at the nucleic acid region assayed. However, the absence of an amplified product in the sample treated with the methylation-sensitive restriction enzyme together with the absence of an amplified product in the sample treated with the isoschizomer of the methylation-sensitive restriction enzyme indicates that no methylation has occurred at the nucleic acid region assayed.

Another method for detecting a methylated CpG-containing nucleic acid comprises the steps of: bringing a nucleic acid-containing sample into contact with an agent that modifies unmethylated cytosine; and amplifying the CpG-containing nucleic acid in the sample using CpG-specific oligonucleotide primers, wherein the oligonucleotide primers distinguish between modified methylated nucleic acid and non-methylated nucleic acid and detect the methylated nucleic acid. The amplification step is optional and desirable, but not essential. The method relies on the PCR reaction to distinguish between modified (e.g., chemically modified) methylated DNA and unmethylated DNA. Such methods are described in U.S. Pat. No. 5,786,146 relating to bisulfate sequencing for detection of methylated nucleic acid.

In another embodiment, the method for detecting a methylated nucleotide comprises whole genome (Methylated DNA immunoprecipitation) MeDIP-seq. Such methods are described in Down et al. (2008, Nat Biotechnol 26:779-85) and Jacinto et al., (2007, Biotechniques 44:35-9).

In another embodiment, the methylation status of the phenotypic variation markers may be detected along with other markers in a multiplex or panel format. Markers are selected for their predictive value alone or in combination with the gene fusions.

The methylation levels of non-amplified or amplified nucleic acids can be detected by any conventional means. In other embodiments, the methods described in U.S. Pat. Nos. 7,611,869, 7,553,627, 7,399,614, and/or 7,794,939, each of which is herein incorporated by reference in its entirety, are utilized. Additional detection methods include, but are not limited to, bisulfate modification followed by any number of detection methods (e.g., probe binding, sequencing, amplification, mass spectrometry, antibody binding, etc.) methylation-sensitive restriction enzymes and physical separation by methylated DNA-binding proteins or antibodies against methylated DNA (See e.g., Levenson, Expert Rev Mol Diagn. 2010 May; 10(4): 481-488; herein incorporated by reference in its entirety).

In some embodiments, a computer-based analysis program is used to translate the raw data generated by the detection assay (e.g., the presence, absence, or amount of methylation of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine or fecal sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., methylation data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence or absence of aberrant methylation) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular phenotype or as a companion diagnostic to determine a particular phenotype.

Compositions for use in the diagnostic methods described herein include, but are not limited to, probes, amplification oligonucleotides, detection reagents, controls and the like. In some embodiments, reagents are provided in the form of an array.

Diagnostic

One aspect of the present invention relates to a method of identifying a phenotype associated with an differential methylation of DNA in a sample from a subject by measuring the methylation level of one or more DNA biomarkers from a test sample in comparison to that of a normal or standard sample, wherein the fold difference between the methylation level of the test sample in relation to that of the normal/standard sample indicates the likelihood of the test sample having the phenotype.

The differential methylation is referred as hypermethylation and/or hypomethylation (e.g., demethylation). In a preferred embodiment, the abnormal methylation is hypermethylation. In another preferred embodiment, the abnormal methylation is hypomethylation.

The methylation of DNA can be detected via methods known in the art and those described elsewhere herein. In one embodiment, the level can be measured via a methylated-CpG island recovery assay (MIRA), combined bisulfite-restriction analysis (COBRA) or methylation-specific PCR (MSP). In another preferred embodiment, the methylation levels of a plurality DNA can be measured through MIRA-assisted DNA array. In yet another embodiment, the methylation levels of a plurality DNA can be measured using MeDIP-seq.

The biomarkers are fragments of genome DNA that contain a CpG island or CpG islands, or alternatively, are susceptible to aberrant methylation. Examples of the DNA markers associated with a condition are disclosed elsewhere herein. Specifically, examples of the DNA markers include but are not limited to DMR377, DMR386, DMR233, DMR352, DMR378, DMR379, DMR367, DMR383, DMR350, DMR384, HORMAD2, SECTM1A, LOC781977, LOC10033649, LOC100300790, CD7, and LOC10190343.

In another embodiment, the method of present invention is directed to a method of identifying a phenotype in a test subject or a test sample through determining the methylation level of DNA markers from the test subject or test sample in relative to the level of the DNA markers from a normal subject or sample, wherein the DNA markers are selected from one or more of DMRs in table 2. In another embodiment the DNA marker is one or more genes selected from the group consisting of DMR377, DMR386, DMR233, DMR352, DMR378, DMR379, DMR367, DMR383, DMR350, DMR384, HORMAD2, SECTM1A, LOC781977, LOC10033649, LOC100300790, CD7, and LOC10190343.

It is contemplated that the biomarkers for altered methylation according to the present invention have the following criteria. An altered methylation status that identifies a phenotype can include a decreased methylation status relative to a control sample from a subject that does not have the phenotype (e.g., a population average of samples, a control sample, a prior sample from the same subject, etc.). In another embodiment, an altered methylation status that identifies a phenotype can include an increased methylation status relative to a control sample from a subject that does not have the preferred phenotype (e.g., a population average of samples, a control sample, a prior sample from the same patient, etc.). Accordingly, the invention in some instances provides a combination of markers for phenotypic variation, wherein some of the markers include decreased methylation of a gene or gene regulatory region and other markers include increased methylation of a gene or gene regulatory region.

In one embodiment, the present invention provides a method of identifying a high milk yield livestock. Accordingly, the method comprises determining the level of methylation of a biomarker in a biological sample of a livestock, comparing the level of methylation of the biomarker in the sample of the livestock with a comparator control, and identifying the livestock as being a high yield livestock based on whether the level of methylation of the biomarker is higher or lower than the level of methylation of the comparator control.

In another embodiment, the present invention provides a method of monitoring milk productivity in a livestock. In some embodiments, the method comprises determining the level of methylation of a biomarker in a biological sample of a livestock at regular intervals, comparing the level of methylation of the biomarker in the sample of the livestock to a comparator control or a previous level of methylation of the biomarker, and identifying a change in milk productivity based on whether the level of methylation of the biomarker is higher or lower than the level of methylation of the previous level.

In yet another embodiment, the invention provides a method of selecting a livestock to be culled when its milk production declines. In some embodiments, the method comprises determining the level of methylation of a biomarker in a biological sample of a livestock at regular intervals, comparing the level of methylation of the biomarker in the sample of the livestock to a comparator control or a previous level of methylation of the biomarker, identifying a change in milk productivity based on whether the level of methylation of the biomarker is higher or lower than the level of methylation of the previous level, and culling the livestock when the change in milk productivity is negative.

As apparent from the examples disclosed herein, diagnostic tests that use the biomarkers of the invention exhibit a sensitivity and specificity of at least 75%, at least 80%, at least 85%, at least 90%, at least 95%, at least 98% and about 100%. In some instances, screening tools of the present invention exhibit a high sensitivity of at least 75%, at least 80%, at least 85%, at least 90%, at least 95%, at least 98% and about 100%.

In one embodiment, analysis of one of the genes or genomic sequence is selected from one or more DMR in table 2. In another embodiment, analysis of one of the genes or genomic sequence is selected from the group consisting of DMR377, DMR386, DMR233, DMR352, DMR378, DMR379, DMR367, DMR383, DMR350, DMR384, HORMAD2, SECTM1A, LOC781977, LOC10033649, LOC100300790, CD7, and LOC10190343, and any combination thereof enables for detecting, or detecting and distinguishing a preferred phenotype.

The present invention enables identification of events that are advantageous in which important genetic and/or epigenetic parameters within at least one gene or genomic sequence selected from one or more DMR in table 2. In some embodiments, the gene or genomic sequence is selected from the group consisting of DMR377, DMR386, DMR233, DMR352, DMR378, DMR379, DMR367, DMR383, DMR350, DMR384, HORMAD2, SECTM1A, LOC781977, LOC10033649, LOC100300790, CD7, and LOC10190343, and any combination thereof may be used as markers. The parameters obtained by means of the present invention may be compared to another set of genetic and/or epigenetic parameters, the differences serving as the basis for a diagnosis and/or prognosis of events that are disadvantageous to patients or individuals.

In one embodiment, the present invention provides for identification of phenotypic variation based on measurement of differential methylation status of one or more dinucleotide sequences of at least one genomic region selected from one or more DMR of table 2. In another embodiment, identification of phenotypic variation is based on measurement of differential methylation status of one or more dinucleotide sequences of at least one the group consisting of DMR377, DMR386, DMR233, DMR352, DMR378, DMR379, DMR367, DMR383, DMR350, DMR384, HORMAD2, SECTM1A, LOC781977, LOC10033649, LOC100300790, CD7, and LOC10190343, and any combination thereof that comprise such a dinucleotide sequence. Typically, such assays involve obtaining a sample from a subject, performing an assay to measure the methylation state of at least one gene or genomic sequence of a DMR selected from a DMR of table 2. In some embodiments, the genomic region is selected from the group consisting of DMR377, DMR386, DMR233, DMR352, DMR378, DMR379, DMR367, DMR383, DMR350, DMR384, HORMAD2, SECTM1A, LOC781977, LOC10033649, LOC100300790, CD7, and LOC10190343, and any combination thereof, preferably by determining the methylation status of at least one gene selected from the group consisting of DMR377, DMR386, DMR233, DMR352, DMR378, DMR379, DMR367, DMR383, DMR350, DMR384, HORMAD2, SECTM1A, LOC781977, LOC10033649, LOC100300790, CD7, and LOC10190343, and any combination thereof, derived from the sample, relative to a control sample, or a known standard and making a diagnosis based thereon.

Although diagnostic and identification accuracy and sensitivity may be achieved by using a combination of markers, such as 2 or more biomarkers of the invention, practical considerations may dictate use of one or more biomarkers and smaller combinations thereof. Any combination of markers for a specific phenotype may be used which comprises 1, 2, 3, 4, 5, 6 or more markers. Combinations of 1, 2, 3, 4, 5, 6 or more markers can be readily envisioned given the specific disclosures of individual markers provided herein.

Kits

In one embodiment, the present invention provides a kit comprising: a means for determining methylation of at least one biomarker.

In some embodiments, the biomarker is a DMR is selected from one or more genomic regions set forth in table 2.

In another embodiment, biomarker is a genomic region selected from the group consisting of DMR377, DMR386, DMR233, DMR352, DMR378, DMR379, DMR367, DMR383, DMR350, DMR384, HORMAD2, SECTM1A, LOC781977, LOC10033649, LOC100300790, CD7, and LOC10190343, and any combination thereof. In one embodiment, the kit comprises instructions for carrying out and evaluating the described method of methylation analysis.

In a further embodiment, said kit may further comprise standard reagents for performing a CpG position-specific methylation analysis.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Genome-Wide DNA Methylation Patterns and Differential Methylation in Leukocytes from Holstein Cattle with Variable Milk, Fat, and Protein Yield The objective of this study was to identify genome-wide DNA methylation patterns in livestock to provide a resource for further investigation into causes of phenotypic variation in high milk-yield livestock. Moreover, the rapid genetic change in Holsteins provides a model to elucidate how DNA methylation responds to artificial and natural selection.

Briefly, experiments were designed to evaluate the genome-wide DNA methylation patterns in leukocytes from mature Holstein dairy cows with variable milk yield. A geometric mean reads (GMR) were derived to describe methylation across the genome and near gene bodies. Features of the bovine leukocyte methylome are consistent with those reported for other species, including the presence of partially methylated domains (PMD) and the identity of genes located within PMD. High GMR upstream and across first exons was associated with reduced gene expression in an independent population of cattle, whereas genes located within PMD had reduced expression. Differentially methylated regions between high milk yield cows and their control was identified, one of which was associated with an immune related gene family (SECTM1) previously reported to have undergone positive Darwinian selection in cattle when compared to other species. This reference methylome for high producing Holstein cattle provides a resource to more fully evaluate relationships between variation in DNA methylation and phenotype. Unraveling the interactions of DNA methylation with variation in species that have undergone intense artificial selection provides insights into the role that DNA methylation plays in populations subject to natural and artificial selection.

The materials and methods employed in this example are now described.

Material and Methods

Animals and Blood Samples

Ten ml of whole blood was obtained from the coccygeal vein (Penn State Institutional Animal Care and Use Committee protocol number 28889) of 6 lactating Holstein dairy cows located on 4 commercial Pennsylvania dairy farms and from 2 lactating Holsteins at the Penn State University Dairy Research and Teaching Center. The buffy coat was extracted and stored (−20° C.) until DNA was extracted with a DNeasy® Blood & Tissue Kit (QIAGEN Sciences, Germantown, Md.) per manufacturer instructions.

MeDIP-Seq and Geometric Mean Reads

MeDIP-seq was conducted. Library construction consisted of genomic DNA fragmentation (100-500 bp by sonication), 3'-A overhang and ligation of sequencing adaptors, denaturing of double-stranded DNA, immunoprecipitation via 5-mC antibody, and PCR amplification and size selection (200-300 bp, including adaptor sequence). Approximately 100 million paired-end reads of 49 bp in length were generated for each cow.

The reads were aligned to the current bovine assembly (UMD_3.1, http://www.ncbi.nlm.nih.gov/assembly/GCA 000003055.4). Median quality scores ranged from 29 to 31 and the number of reads per nucleotide (RPN) was extracted using SAMtools (Handsaker et al., 2009). The geometric mean reads (GMR) was determined as $GMR = e^{mean(ln(NR+1))-ln(2)/8}$. The +1 term was added so that the natural log could be derived for cows with no reads at a given nucleotide and the −ln(2)/8 partly removes the +1 term and sets GMR=1 if a single cow has a single read at a nucleotide. GMR was set to 0 if all 8 cows had no reads at a given nucleotide.

Statistical Analysis

Figure 5:
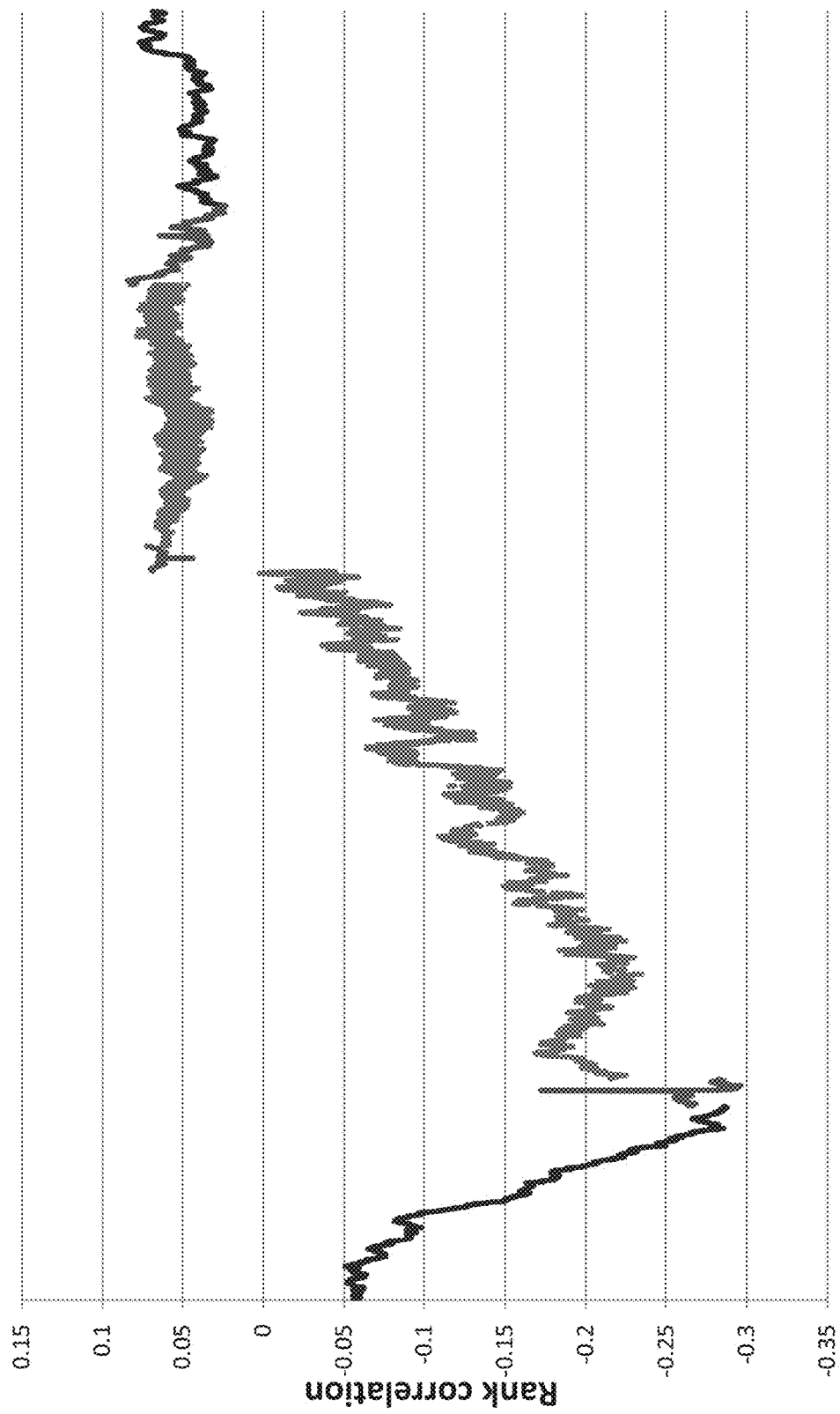
FIG. 5 depicts the spearman rank correlation between geometric mean reads and gene expression in an independent population of Holsteins (Huang et al., 2012) for 1 kb upstream and 1 kb downsteam (blue); first, middle, and last exons (red); and first and last introns (gray) for 9,750 Ensembl genes with expression data available.
Figure 6A:
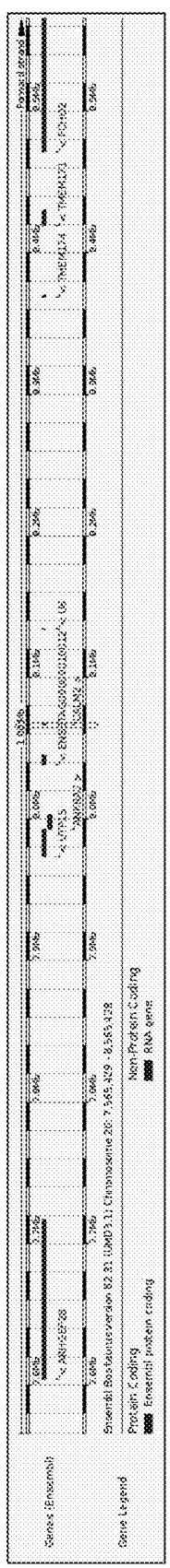
FIG. 6A and FIG. 6B, depicts DMR 386. This DMR is 1692 bp upstream of a gene (ENSBTAG00000032705; CALM2) on the positive DNA strand.
Figure 6B:
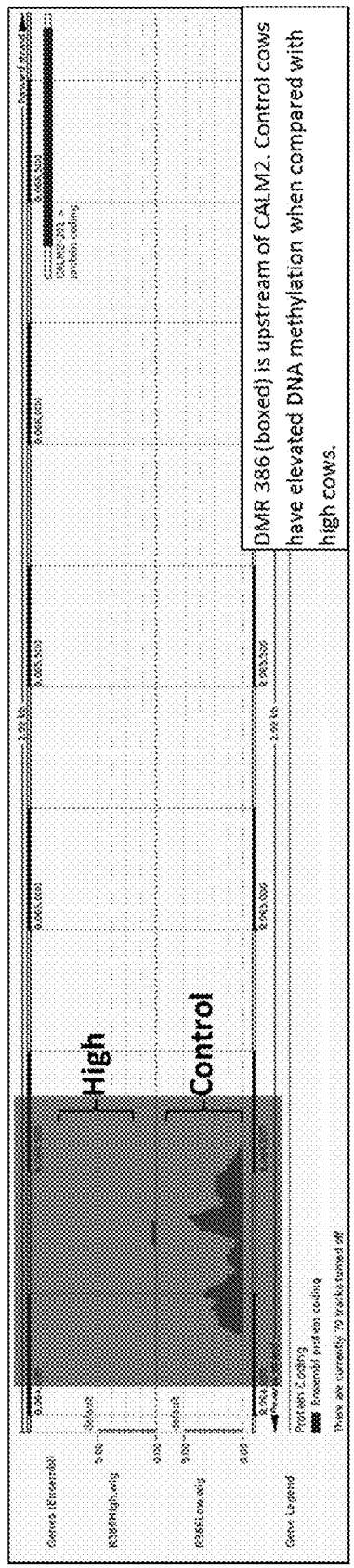
Figures 7A, 7B:
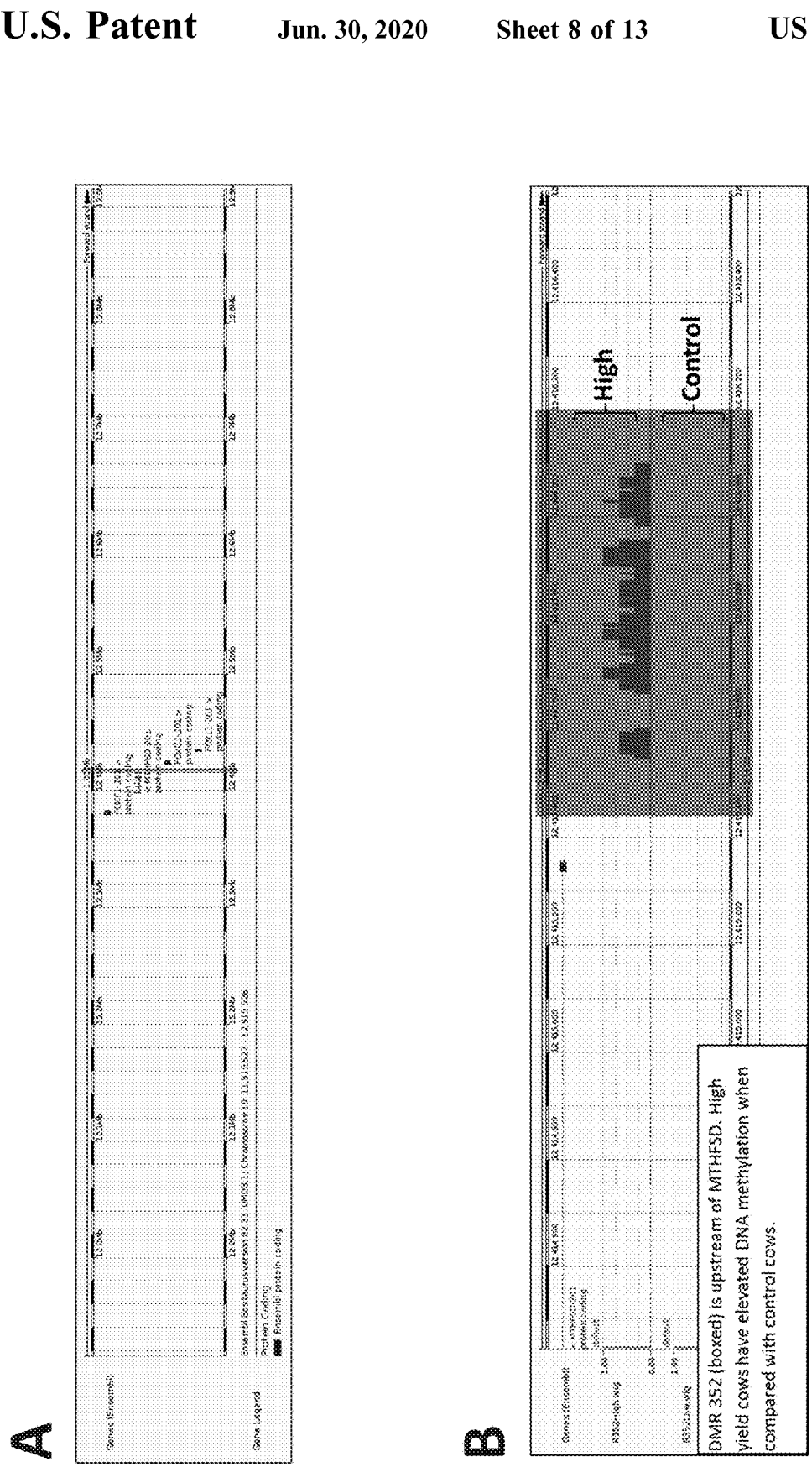
FIG. 7A and FIG. 7B, depicts DMR 352. This DMR is 92 bp upstream of a gene (ENSBTAG00000012446; MTHFSD) on the negative DNA strand.
Figure 8A:
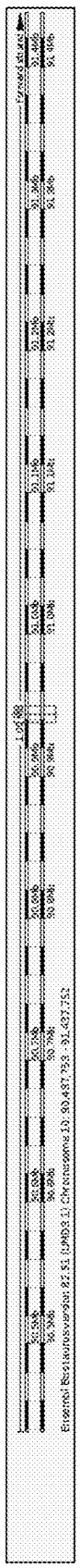
FIG. 8A and FIG. 8B, depicts DMR 233. This long-range regulatory DMR is not associated with annotated features within 100 kb.
Figure 8B:
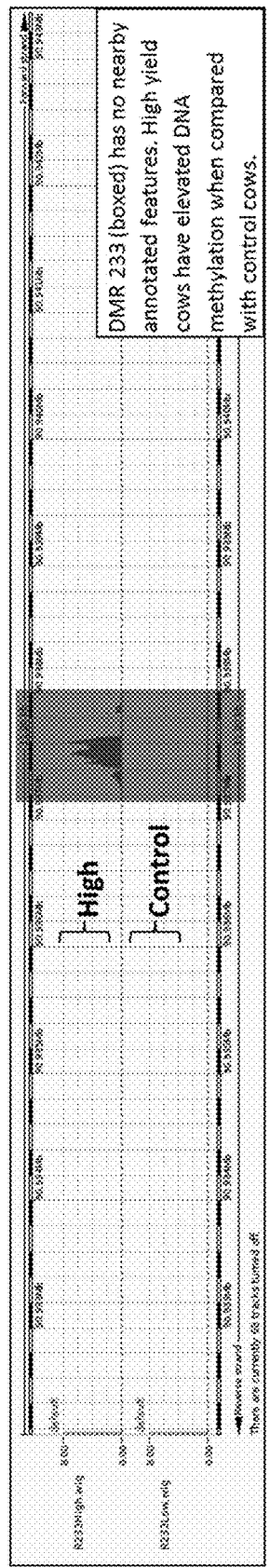
Figure 9A:
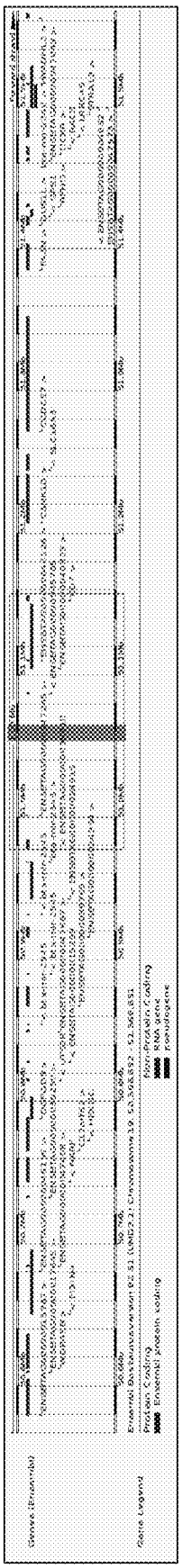
FIG. 9A and FIG. 9B, depicts DMR 378 and 379. These DMR are in close proximity to each other in SECTM1 region of BTA 19. They directly overlap the Secreted and Transmembrane Protein 1-like pseudogene (NCBI Reference Sequence database LOC100300790), are near copies of SECTM1 protein coding genes and additional pseudogene and miRNA transcripts.
Figure 9B:
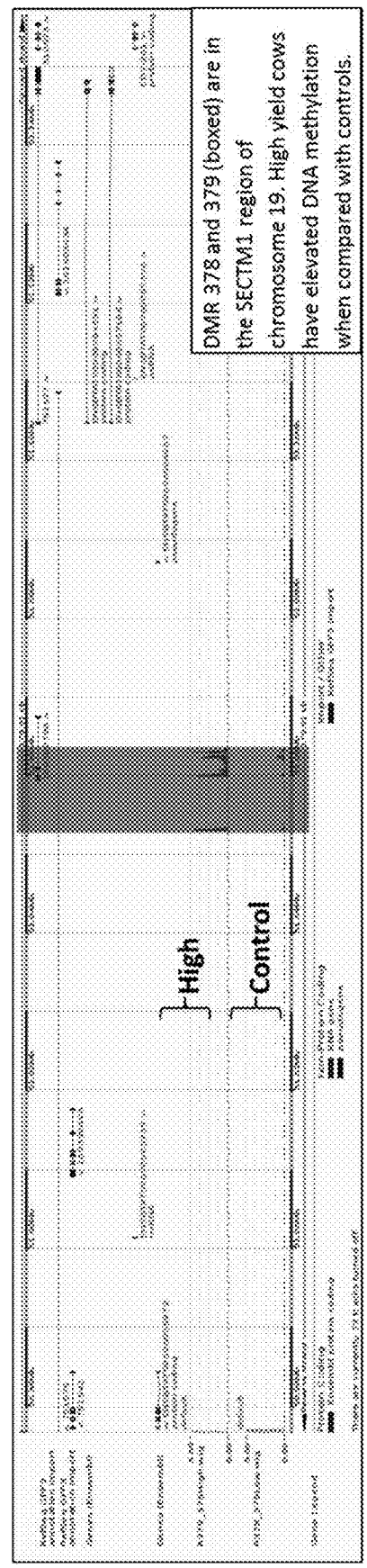
Figure 10A:
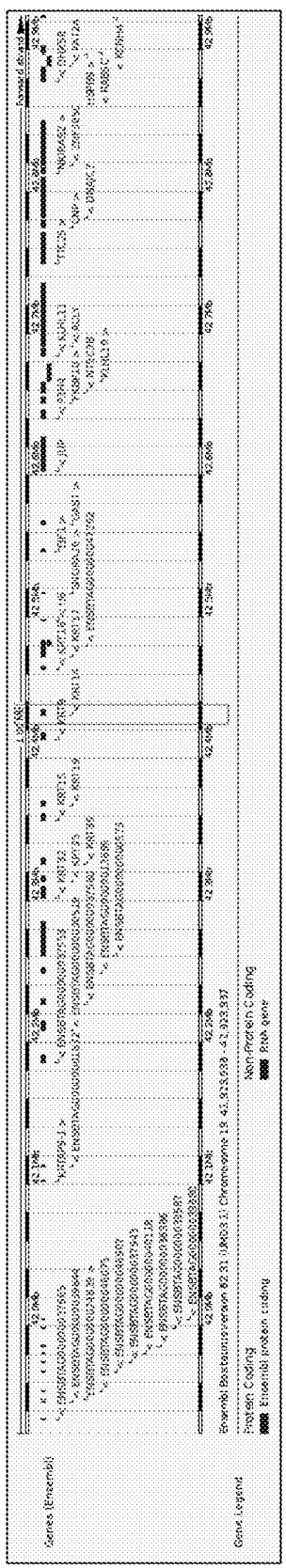
FIG. 10A and FIG. 10B, depicts DMR 377. This DMR is in the proximity of the KRT family of genes, including 3146 bp downstream of ENSBTAG00000007583 (KRT14).
Figure 10B:
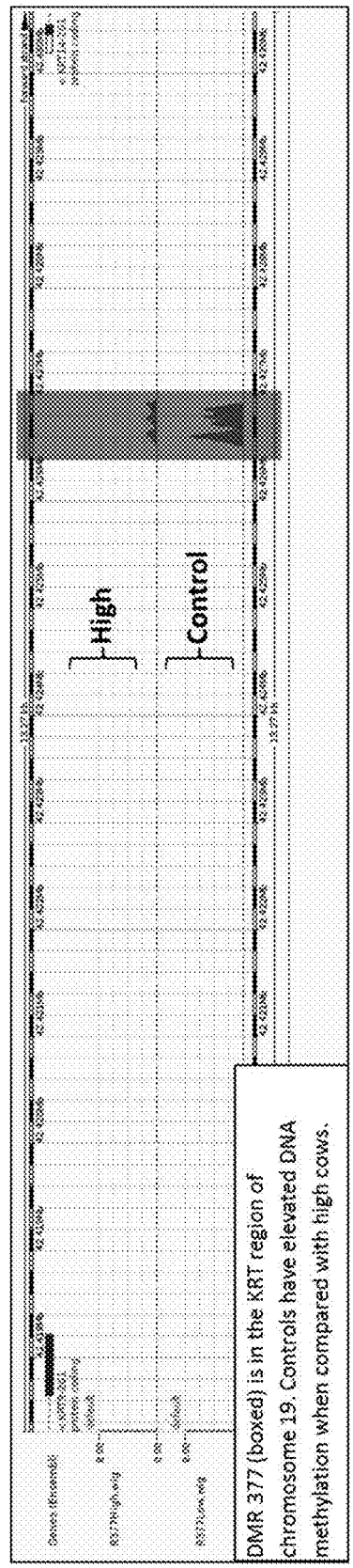
Figure 11A:
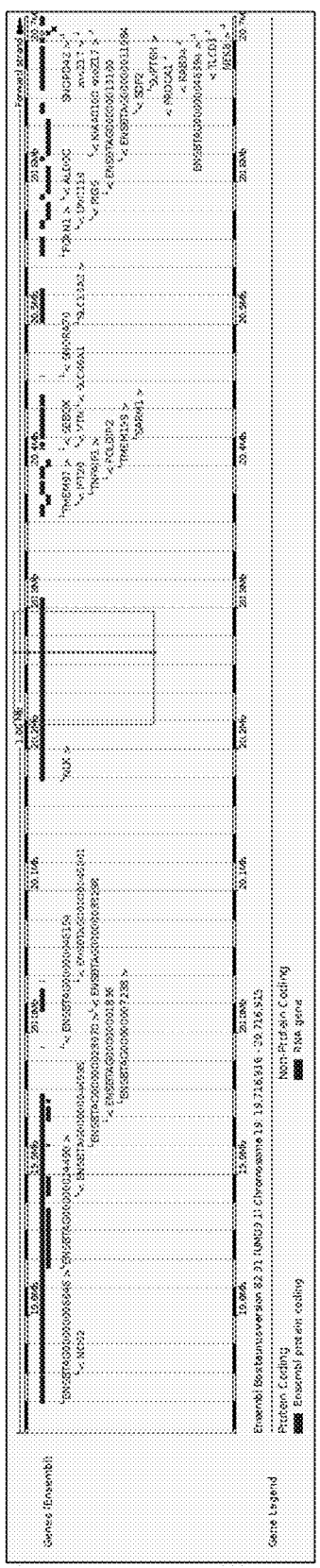
FIG. 11A and FIG. 11B, depicts DMR 367. This is an intragenic DMR that is located within an intron of ENSBTAG00000014825 (NLK).
Figure 11B:
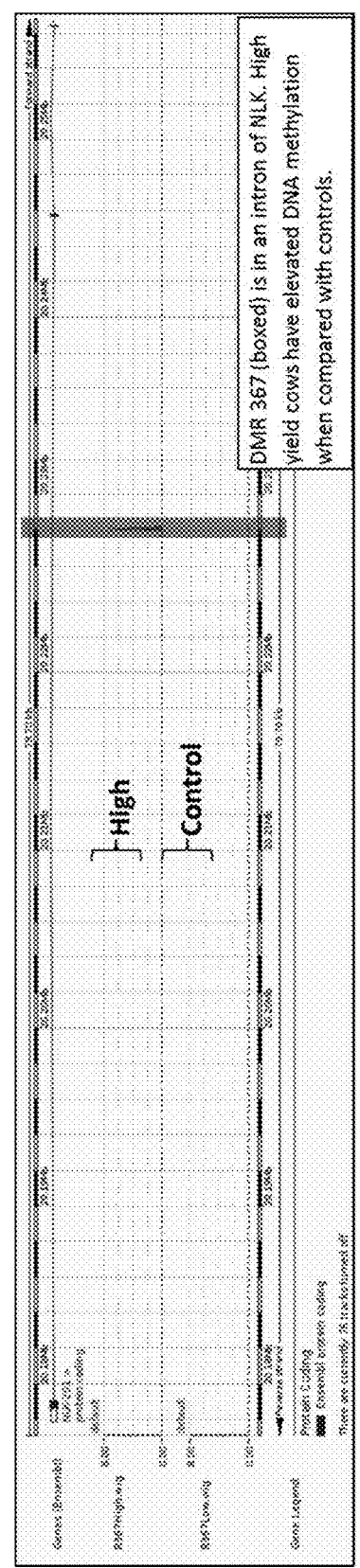
Figure 12A:
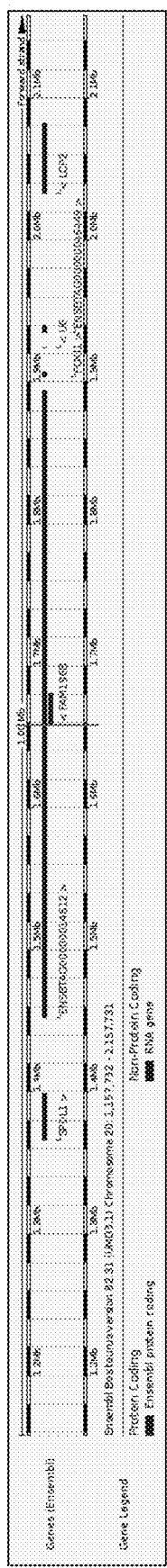
FIG. 12A and FIG. 12B, depicts DMR 383. This DMR is located within two protein-coding genes. ENSBTAG0000000213 (FAM196B) is located on the negative DNA strand and an uncharacterized protein-coding gene (ENSBTAG00000014612) is on the positive DNA strand.
Figure 12B:
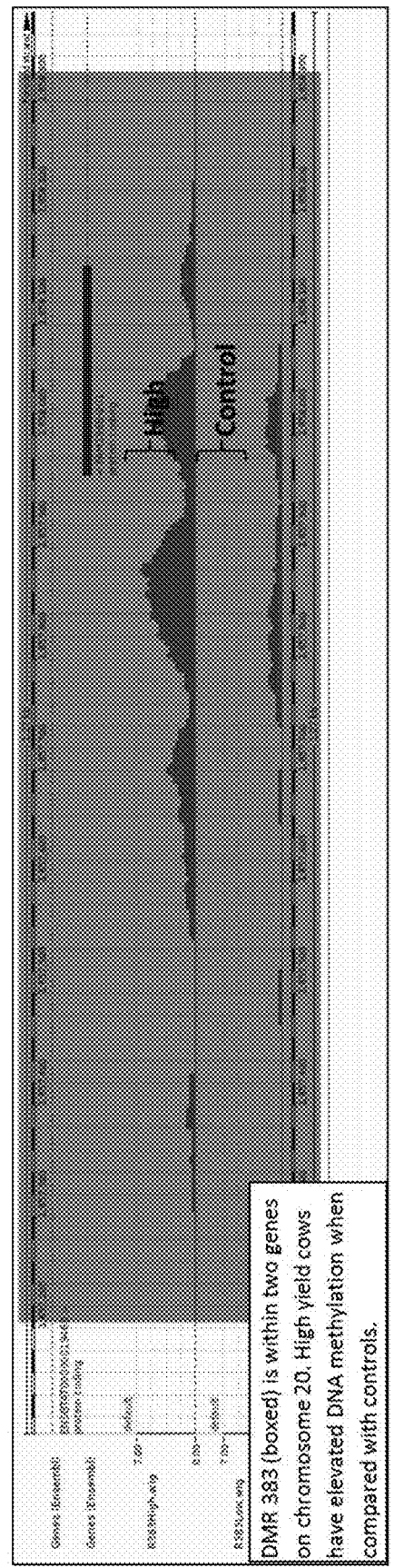

Statistical analyses were performed with SAS (v 9.4; SAS Institute Inc., Cary, N.C.). Differences in μGMR between the centromeric ends, middle, and distal ends of chromosomes were evaluated with the TTEST procedure. Likewise, tests of heterogeneous variance between the centromeric ends, middle, and distal ends of chromosomes were evaluated with the TTEST procedure. The Spearman rank correlation between the number of genes per Mb and μGMR across the same Mb was calculated with the CORR procedure, as were Spearman rank correlations between GMR and gene expression as depicted in FIG. 5.

A relative standardized fold change was derived to identify differentially methylated regions (DMR) for case versus control cows because t-tests identified regions with low variation among cows as significant even if the differences between case and controls were minimal. A standardized change was used because cows may have zero reads in a region preventing direct calculation of the ratio between case and control cows. The $log_2$ of the total number of reads in a region was determined for each cow and then standardized within cow to a mean of 100 and standard deviation of 5. The ratio of each case to their control from the same herd was determined, and the mean ratio of the three pairs derived. A permutation test was conducted with 0.2% of nucleotides randomly drawn and standardized reads for the region (n=1,650,876 regions sampled) determined for both members of a case-control pair. The ratio of standardized reads was determined and merged with randomly drawn regions for the other pairs. The permutations were used to derive the expected mean ratio (1.00) and standard deviation (0.028) which was used to determine the P-Value for the observed fold changes. The process was reversed and the ratio of control to case cows determined, with P-Values multiplied by 2 to account for the two-tailed aspect of the test. All P-values were then evaluated with the MULTTEST procedure of SAS to derive the False Discovery Rate (FDR).

A permutation test was also conducted to identify significant partially methylated domains (PMD). The percentage of nucleotides (PCTN) where at least 1 cow had reads was determined for the 10 kb windows described in results. Ten windows were then drawn at random (with replacement) and the maximum PCTN of the ten windows was determined. This process was repeated 1 million times. Based on the permutation test, the maximum PCTN of ten consecutive 10 kb windows was expected to fall below 37.36% for one percent of ≥100 kb windows if methylation levels in adjoining windows are independent. Genomic regions of with maximum PCTN less than this amount were considered significant PMD at P<0.01.

The results of the experiments are now described.

Animals

Blood was collected from the tail (coccygeal) vein of 8 lactating Holstein dairy cows including six cows from four commercial Pennsylvania dairy farms and two cows from the Penn State University Dairy Research and Teaching Center. Six cows represented case-control pairs from two commercial herds and the Penn State herd. The high milk yield cows averaged 18,848 kg of milk during the parity of blood sampling, whereas control cows averaged 13,434 kg of milk. The two remaining cows were selected from separate herds to increase the number of cows and herds represented and had milk yield that was intermediate (16,236 kg) to the high and control cows. Identifying cows with extremely high milk yield required that sampling of cows from generally well-managed herds; consequently, control cows had milk yield that was somewhat higher than the national average of 11,192 kg for Holsteins (Norman and Walton, 2014).

Figure 1B:
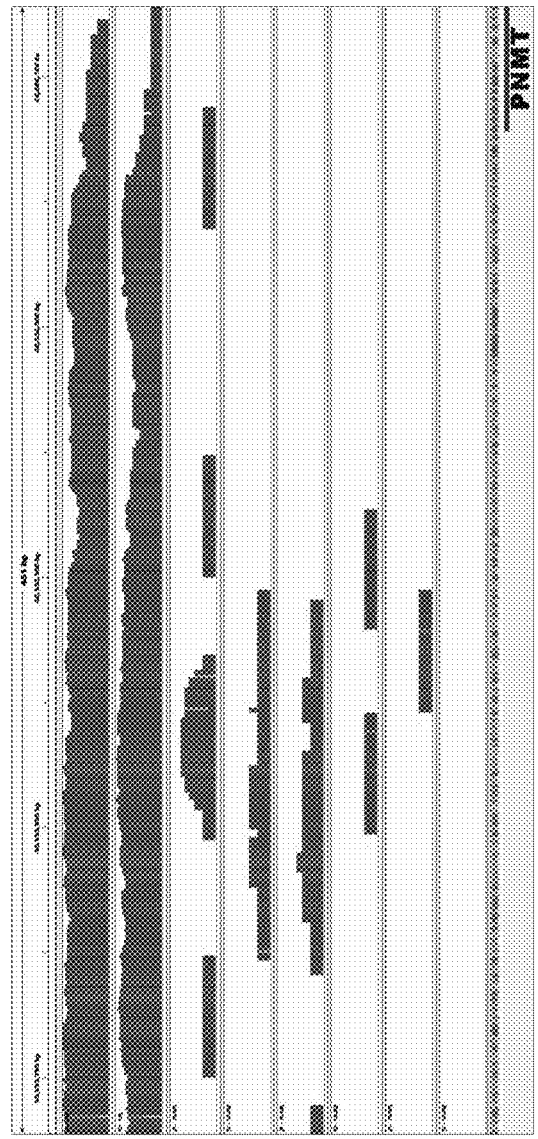
Figures 1C, 1D:
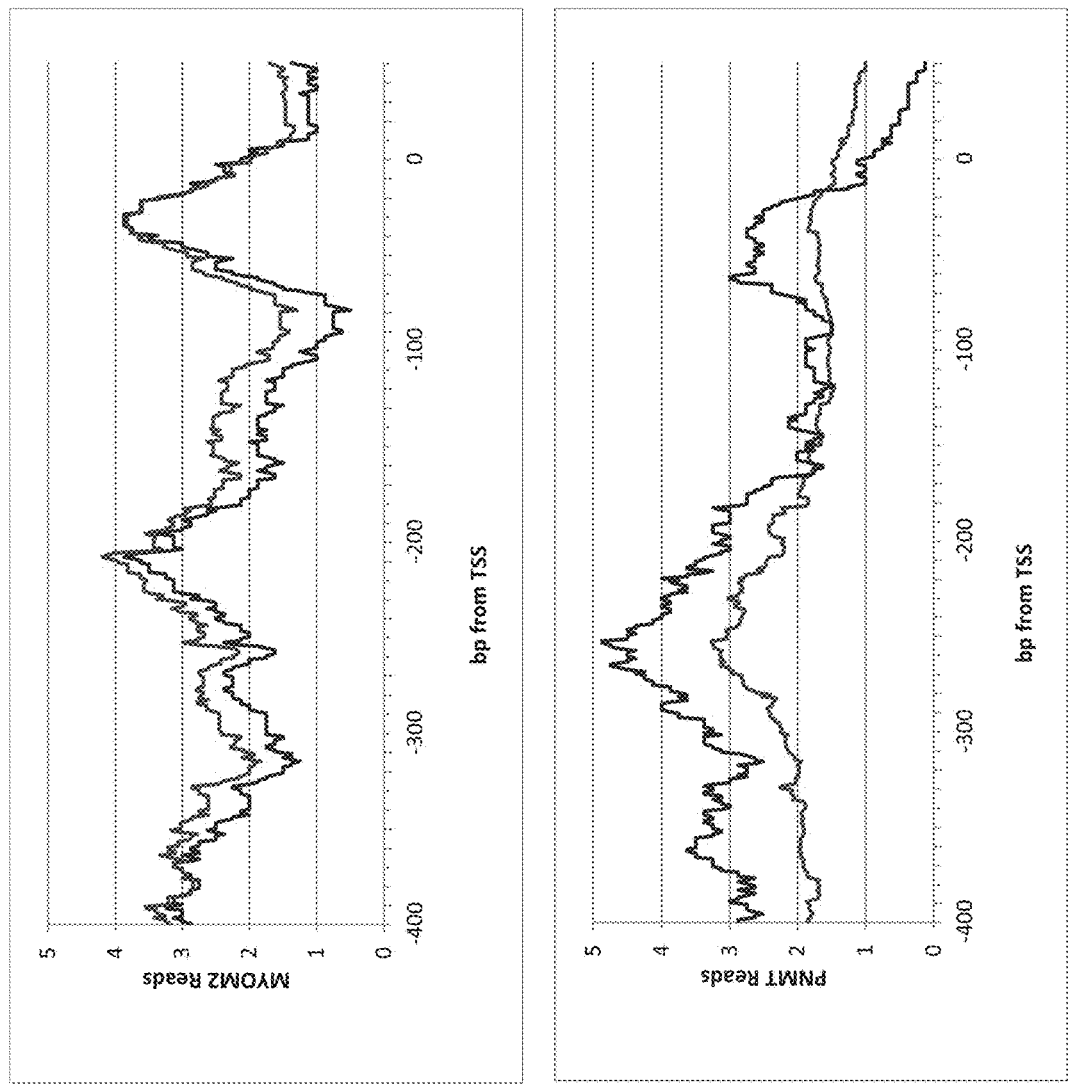

Geometric Mean Reads (GMR) and General Methylation Patterns in the Genome of Holstein Cows Following a visual inspection of results (Integrative Genomics Viewer; Robinson et al., 2011; Thorvaldsdóttir et al., 2012) and considering preliminary descriptive statistics, it was clear that reads were not normally distributed across cows or genomic regions. Therefore, geometric mean reads (GMR) were derived on a per nucleotide basis to describe general methylation patterns for this group of animals as described above. FIG. 1 demonstrates alignment reads from 400 bp upstream to 50 bp downstream of the transcription start site (TSS) for a gene (MYOM2) where all cows had similar number of reads and a second gene (PNMT) with more variation among cows. The number of reads per nucleotide (RPN) was calculated and summed for the range shown in FIG. 1. The range was 313 to 1475 with an average of 962 across the 8 cows for MYOM2. The mean (1148) was similar for PNMT, but the range (0 to 4464) was much higher. The average RPN is higher for PNMT (2.54) than for MYOM2 (2.13); however, six of the eight cows had more reads for MYOM2. The average GMR (μGMR) reflects that the majority of cows had more reads for MYOM2 (μGMR=2.56) than for PNMT (μGMR=1.92).

GMR of 13,677 unique *Bos taurus* (BTA) Ensembl genes (release 71; Flicek et al., 2013) with completed coding sequence start and end coordinates were analyzed. μGMR for 1 kb upstream; first, middle and last exons; first and last intron; and 1 kb downstream are presented in FIG. 2 for the 13,677 Ensembl genes. Exon lengths were standardized to the median exon length, which were 159 bp for first exons, 128 bp for all middle exons, and 503 bp for last exons. If there were more than 159 bp for the first exon, the first 79 bp were classified as nucleotides 1 to 79, the last 79 bp were classified as 81 to 159, and all others were classified as nucleotide 80. If there were fewer than 159 bp, the first 50% of nucleotides were associated with the first nucleotides of the exon, whereas the last 50% were associated with the last nucleotides of the exon. The same approach was used for the other exons and introns, with median intron lengths of 2616 bp for first introns and 1343 bp for last introns.

Reads were generally low in the upstream region with the nadir μGMR occurring at 95 bp upstream of the TSS. μGMR was lower in the first exon than in later exons, particularly in the first half of initial exons. The middle exon tended to be most highly methylated, whereas the last exons were generally highly methylated at the beginning of the exon and had lower methylation in the second half of the exon. μGMR were highest for introns near the intron-exon junctions and were lowest in the middle and declined downstream as the distance from the gene increased.

Differentially Methylated Regions in Case Versus Control Cows

There were 500 differentially methylated regions (DMR) with FDR<0.05 that were identified by determining the fold change in a standardized number of reads in case versus control cows as described in the methods. The most significant DMR spanned an 830 bp region on BTA10 and was not located in close proximity (>500 kb) to annotated genes.

Figure 3:
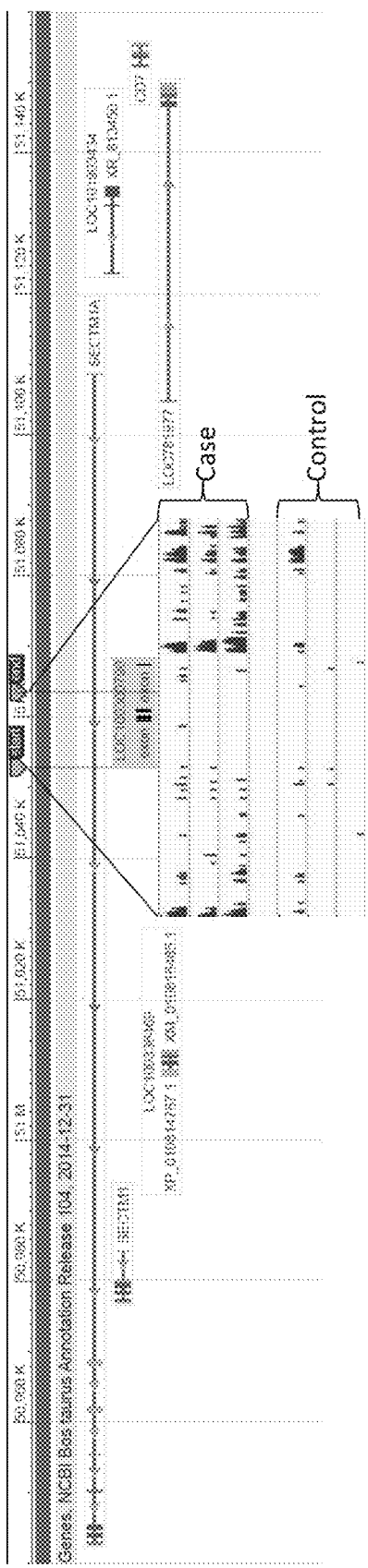
FIG. 3 depicts the annotation of the SECTM1 region of BTA 19 (50,940K to 51,160K) with alignments (Integrative Genomics Viewer; Robinson et al., 2011; Thorvaldsdóttir et al., 2012) of case and control cows for two neighboring DMR. The inset demonstrates the location of the DMR which are aligned to LOC100300790, Secreted and Transmembrane Protein 1-like. The first DMR starts at base 51,052,906 and ends at base 51,053,519, whereas the second is from 51,059,764 bp to 51,063,463 bp.
Figure 4:
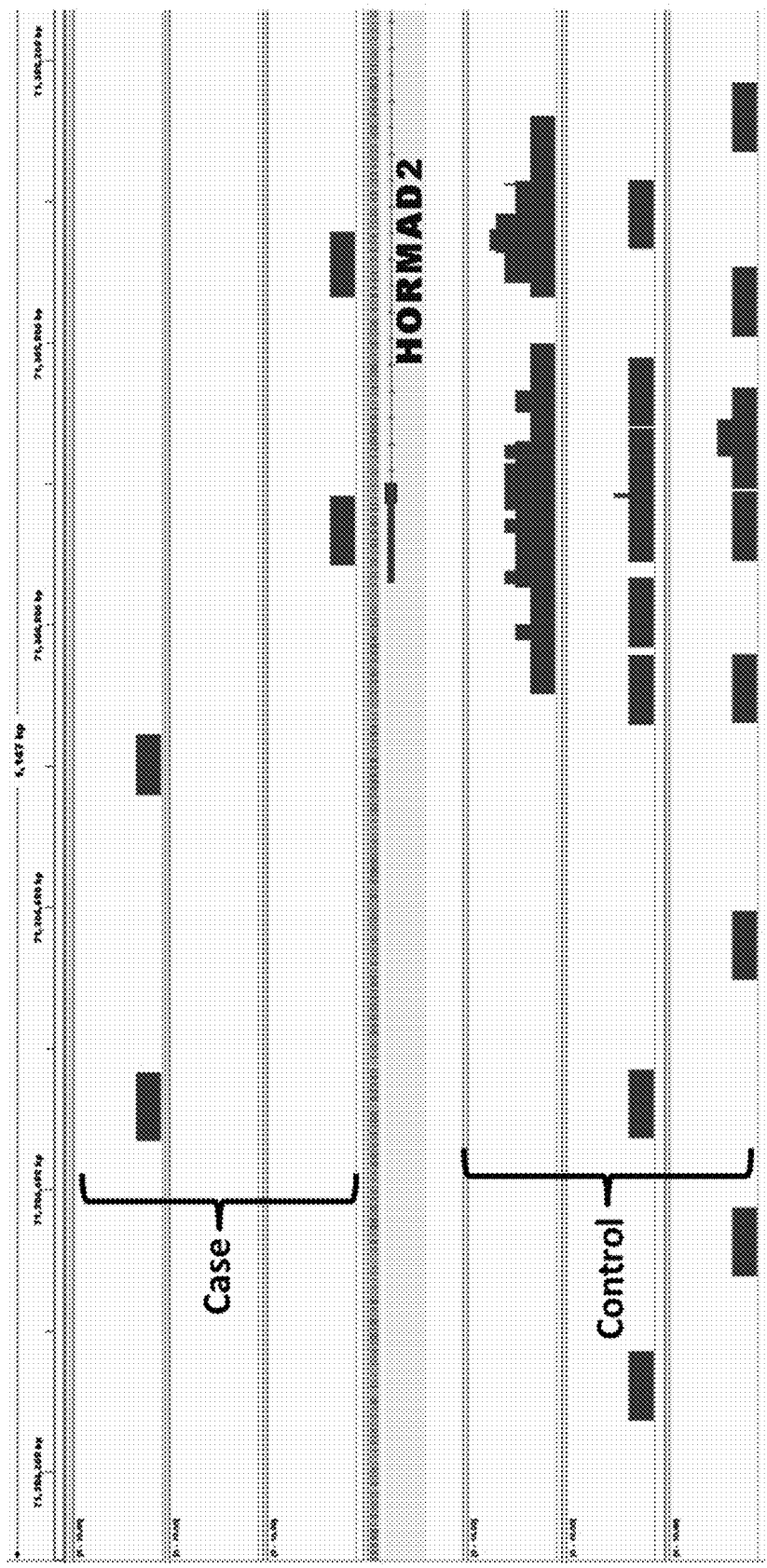
FIG. 4 depicts the alignments (Integrative Genomics Viewer; Robinson et al., 2011; Thorvaldsdóttir et al., 2012) for case (top 3 panels) and control (lower 3 panels) cows for a DMR at the beginning of HORMAD2 on BTA17.

The second and third most significant DMR were located in close proximity on BTA19 and are shown in FIG. 3 (Integrative Genomics Viewer; Robinson et al., 2011; Thorvaldsdóttir et al., 2012) with their broader genomic region. This region harbors members of the Secreted and Transmembrane Protein 1 (SECTM1) gene family. The DMR resides in SECTM1A and directly covers an embedded pseudogene (LOC100300790, Secreted and Transmembrane Protein 1-like). LOC781977 (secreted and transmembrane 1-like) and LOC100336469 (secreted and transmembrane protein 1A) are also members of the SECTM1 family. An uncharacterized ncRNA LOC101903434 and the Cluster of Differentiation 7 (CD7) gene are also located in the region. An additional DMR shown in FIG. 4 covers the first exon of the HORMA domain containing 2 (HORMAD2) gene on BTA17, and had higher levels in the control cows than in the case cows.

Methylation Patterns and Gene Expression in Holstein Leukocytes

μGMR for the Ensembl genes was merged with expression of the Holstein leukocyte transcriptome (GEO accession GSE48487; Huang et al., 2012) with data from 9,750 genes successfully merged. The rank correlation of μGMR on a nucleotide basis with expression in the leukocyte transcriptome is presented in FIG. 5. The correlation between GMR and gene expression became increasing negative from 1 kb until ~35 bp upstream of the TSS. Higher methylation levels across the first exon and in the beginning of the first intron were also associated with lower levels of expression. Methylation levels for the remainder of the gene region had a neutral to slightly positive association with expression levels.

Genome Wide Methylation Patterns and Partially Methylated Domains (PMD)

μGMR in non-overlapping 10 kb windows was determined to evaluate genome wide methylation patterns for all chromosomes. Visually, there appeared to be fewer reads mapped to the centromeric ends of many chromosomes than mapped to the remainder of the chromosome. μGMR in the first 500 kb of the centromeric end (0.26±0.23) were less (P<0.001) than the last 500 kb of the distal end (0.51±0.27) and middle of the chromosomes (0.47±0.08). μGMR for the distal end and middle of the chromosomes were not different, but μGMR was significantly less variable for middle of the chromosomes than for the centromeric and distal ends (P<0.001). There were also large differences among chromosomes with the lowest for the X chromosome (μGMR=0.20) and BTA6 (μGMR=0.37), whereas BTA19 had the highest rate (μGMR=0.63).

The number of Ensembl genes in non-overlapping 1 Mb windows was determined and overlaid on the genome wide methylation distribution shown in the supplementary information. The Spearman rank correlation between μGMR across 1 Mb windows with the number of Ensembl genes in the window was 0.46 (P<0.0001), indicating that higher gene density was associated with higher μGMR.

Genomic regions with suppressed levels of methylation have been described as PMD (Miniou et al., 1997), and such regions were apparent when evaluating μGMR across 10-kb windows. A permutation test was used to empirically identify PMD of 100 kb or larger. There were 3051 PMD covering 726 Mb (~27%) of the genome identified, with 25% of autosomes and 70% of the X chromosome falling within a PMD. The largest single PMD was from 43.06 to 47.65 Mb on the X chromosome, whereas the largest autosomal PMD stretched from 73.20 to 76.77 Mb on BTA12.

Partially Methylated Domains and Gene Functions in Holstein Leukocytes

There were 1463 genes located in significant PMD, including 1218 autosomal genes and 245 on the X chromosome. This represented 9.3% of the 13,156 autosomal genes and 47% of the X genes. Of the genes located within a PMD, 649 were included in the 9,750 genes with expression data available. Expression (1=expressed, 0=not expressed) of genes located within PMD were compared to non-PMD genes. The odds of expression for genes not in a PMD (n=9104) compared with those within a PMD were 1.66:1, which was highly significant (P<0.001).

Figure 2:
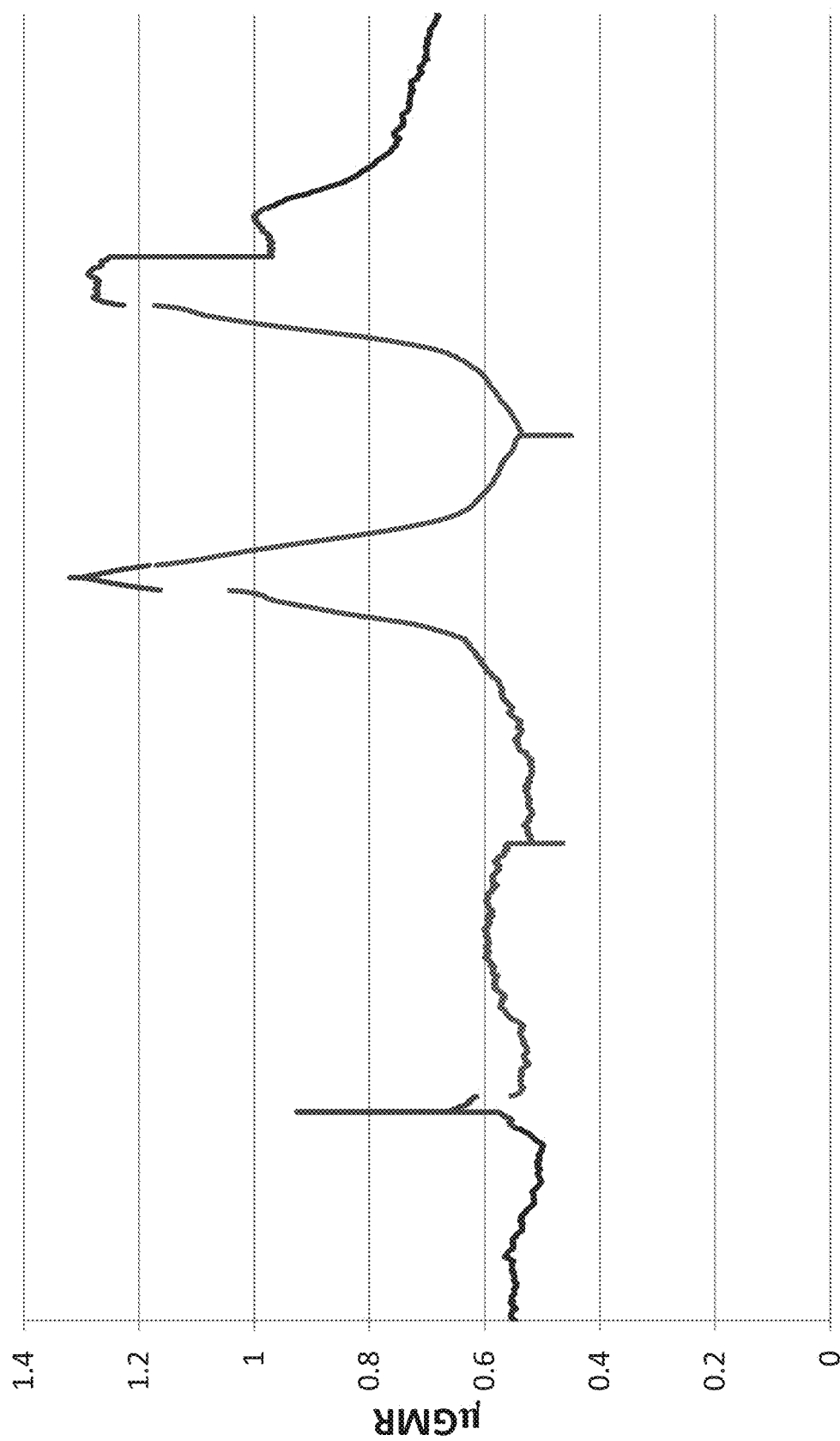
FIG. 2 depicts the average geometric means reads (µGMR) 1 kb upstream and 1 kb downsteam (blue); first, middle, and last exons (red); and first and last introns (gray) for 13,677 Ensembl genes.

The PMD genes were submitted to DAVID (Huang et al., 2009a; 2009b) for functional evaluation with 1178 matching known genes (185 X-linked genes) in the DAVID system. The background genes were the 13,677 Ensembl genes. There were six significant (Bonferroni adjusted P-Value<0.05) functional annotation charts and all were part of a single annotation cluster (medium classification stringency) with an enrichment score of 19.97, which corresponds to a geometric mean Fisher Exact P-Value of 5.8× $10^{-18}$ (Huang et al., 2007). The annotation charts are reported in Table 1 and encompassed 235 total genes, including 76 genes belonging to the Olfactory Transduction KEGG pathway (Kanehisa et al., 2000; 2014). One additional annotation chart is reported in the table that approached significance (Bonferroni adjusted p=0.062), which was an InterPro (Hunter et al., 2011) MAGE homology domain (IPR002190) of 6 X chromosome genes and 1 autosomal gene with a fold enrichment (FE) of 8.2.

than for MYOM2 (0.41) despite six of the cows having more reads for MYOM2. The higher reads for six of eight cows and more even distribution of reads across cows resulted in higher µGMR for MYOM2 than for PNMT. GMR was reported on a per-nucleotide basis to improve resolution of methylation levels near gene bodies as depicted in FIGS. 2 and 5.

The degree of DNA methylation in Holstein leukocytes levels varied widely across the genome and many features of the cattle methylome are shared with those from other species. The well described decline in promoter methylation (FIG. 2) coupled with an inverse association between promoter methylation and transcription (FIG. 5) was apparent.

Genes with roles in immune function are strong candidates for differential methylation in this study because DNA was isolated from white blood cells. SECTM1 is highly expressed in leukocytes (Slentz-Kesler et al., 1998) and SECTM1 and CD7 are reported to be INF-γ induced co-stimulators of T-cell proliferation (Wang et al., 2012). The SECTM1 gene is also intriguing because humans are

TABLE 1

Significant functional annotation charts (DAVID; Huang et al., 2009a; 2009b) for genes located within partially methylated domains (PMD)

| Term | No. of genes | Bonferroni adjusted P-value | Category | Ontology | Go Term ID |
|---|---|---|---|---|---|
| Olfactory receptor activity | 77 | $4.9 \times 10^{-39}$ | Go Term | Molecular function | GO:0004984 |
| Olfactory transduction | 76 | $2.0 \times 10^{-31}$ | KEGG Pathway | NA | NA |
| GPCR protein signaling pathway | 102 | $9.6 \times 10^{-20}$ | Go Term | Biological process | GO:0007186 |
| Cell surface receptor linked signal transduction | 111 | $1.3 \times 10^{-10}$ | Go Term | Biological process | GO:0007166 |
| Intrinsic to membrane | 202 | $2.2 \times 10^{-3}$ | Go Term | Cellular component | GO:0031224 |
| Integral to membrane | 197 | $1.4 \times 10^{-3}$ | Go Term | Cellular component | GO:0016021 |
| MAGE protein | 7 | $6.2 \times 10^{-2}$ | INTERPRO | NA | NA |

DNA Methylation Patterns and their Correlation to Gene Expression and Function in the Bovine Leukocyte Epigenetic descriptions in high yielding dairy cattle that have undergone intensive genetic selection can serve as a model to examine effects of selection on DNA methylation. DNA methylation in leukocytes was used here because blood is accessible and farmers are unlikely to approve of invasive tissue sampling from the elite, high yielding cows that are of particular interest because they are population outliers. The differences in yield for this population were not attributable to DNA sequence variation. Milk yield for the three case cows was expected to be 527 kg higher than for the three control cows based upon genomic estimated breeding values (https://www.cdcb.us/eval.htm). The actual difference in yield was 5414 kg with case cows producing 40% more milk than control cows.

The method of deriving GMR is described in the methods and was used to describe general methylation patterns because reads are not normally distributed across cows or genomic regions. The advantages of GMR are demonstrated in FIG. 1 for two genes with similar µGMR, but different inter-cow variation. For comparison, a more traditional normalized reads count (NRC) were derived for the region displayed in FIG. 1 as (RC*1,000,000)/(URC) where RC=the number of reads mapped to the region and URC=the total number of unique reads mapped for a cow. The average NRC across these eight cows was higher for PNMT (0.50)

reported to have a single SECTM1 gene whereas there are multiple paralogs in cattle that have undergone positive Darwinian selection (Larson et al., 2006). There was a reported 2.73 fold increase in SECTM1 expression in Angus cattle that were resistant to parasitic infection than in those that were susceptible (Li et al., 2011). Significant SNP and haplotypes for somatic cell score, which serves an indicator of mammary gland infection, have been localized to a region upstream of the SECTM1 DMR in German Holsteins (Abdel-Shafy et al., 2014). SECTM1 was reported to be upregulated in the liver of Holsteins treated with estradiol (Piccinato et al., 2011), a SECTM1 SNP was significantly associated with fatty acid composition in beef cattle (ISHII et al., 2013), and shifts in SECTM1 DNA methylation has been demonstrated in response to nonalcoholic fatty liver disease states in humans (Ahrens et al., 2013). The role of SECTM1 in immune function and associations with performance in cattle are supportive of this region as a potential epigenetic-QTL. The localization of the DMR to a SECTM1 pseudogene is also of interest because of a growing appreciation for the role of pseudogenes in gene regulation (Milligan and Lipovich, 2015) which appears to have cell-type specificity (Siggens and Ekwall, 2014).

The effect of higher methylation in the SECTM1 pseudogene on gene expression levels is not clear, so more straightforward situation is one in which higher levels of methylation in control cows over the first exon of HORMAD2

(FIG. 4) is expected to result in lower levels of expression for control cows. HORMAD2 has been implicated in diverse roles and is upregulated in gonads during meiotic prophase and has roles in DNA repair (Wojtasz et al., 2009). Sequence variation in HORMAD2 has been associated with innate immunity and immunoglobulin A nephropathy (Kiryluk et al., 2013), the onset inflammatory bowel disease (Imielinski et al., 2009), and lung cancer (Zhang et al., 2014).

Methylation was lower across initial exons than later exons, and elevated methylation levels across initial exons were associated with a reduction in gene expression in an independent transcriptome analysis. This supports observations by Brennet et al. (2011) that transcriptional silencing is associated with elevated methylation across the first exon. There is growing evidence that methylation is associated with alternative splicing across tissues (Wan et al., 2013). Gelfman et al. (2013) reported that DNA methylation marks exon boundaries while Maunakea et al. (2013) suggested that DNA methylation may facilitate exon recognition by recruiting methyl CpG binding protein 2 and, subsequently, have roles in maintenance of histone hypoacetylation. High levels of methylation across exons with a rapid decline of intronic methylation as distance from the exon-intron junction increased should be expected if methylation was a key exon marker. This was evident here with average methylation levels in the middle of introns as low as levels observed for the promoter.

Adjacent 10 kb windows were not independent with respect to DNA methylation levels, reinforcing the concept that the genome has domains of elevated and repressed methylation levels. Determining domains that qualify as PMD has been done by visualizing data and determining appropriate cutoffs where readily apparent (Lister et al., 2009), or by developing empirical approaches after visually identifying PMD and using such observations to train models to detect PMD on a genome-wide basis (Schroeder et al., 2011). Here, identification of PMD was based from a permutation test that assumes independence of adjacent regions as the goal is to identify contiguous regions with methylation levels that are consistently lower than what is expected by chance.

Lister et al. (2009) reported that 38.4% of autosomes were covered by PMD in differentiated cells, and 80% of the X chromosome was within PMD consistent with low methylation levels associated with X inactivation. A similar trend is reported here with respect to the proportion of autosomes and the X (25% and 70%, respectively) covered by PMD. Schroeder et al. (2011) reported that PMD were more common in human lung fibroblast cells (41%) than in neuronal cells (19%). In both tissue types, genes associated with the sensory perception of smell were highly enriched in PMD (Schroeder et al., 2011). Olfactory related genes were also found to be enriched in PMD (Table 1), suggesting that PMD may be consistent across species for some genes.

There was a tendency (p=0.062) for MAGE homology domain genes to be enriched in PMD, and most were localized to X chromosome. The X-linked MAGE genes were members of MAGE-A (n=2), MAGE-B (n=3) and MAGE-E (n=1) subfamilies, which are also located on the human X chromosome. The single autosomal gene was a necdin homolog member of the MAGE family that is located on BTA21. Chomez et al. (2001) report expression of MAGE-A and MAGE-B families genes to be absent in normal adult tissues with the exception of the testis. The MAGE genes are reported to be cancer testis antigens (CTA) (Scanlan et al., 2002). DNA methylation is reported to be the primary mechanism regulating their expression in testis and cancer stem cells (Frattaa et al., 2011), and the MAGE-A family are reported to be a potential target for cancer immunotherapy (Sang et al., 2011).

Genes located with PMD are reported to have lower levels of expression (Lister et al., 2009; Schroeder et al., 2011). These results support this general observation. There were a relatively low proportion of genes located within PMD compared with the proportion of the genome that is covered by a PMD due to the positive association between gene density and methylation. Nevertheless, genes not located within a PMD were more likely to be expressed than those that were.

The results presented herein show the general DNA methylation patterns and their correlation to gene expression and function in the bovine leukocyte. Features of the leukocyte methylome are consistent with those reported for other species. Differential methylation in a gene family previously reported to have undergone positive Darwinian selection was evident, and unraveling the interactions of genetic selection and methylation shifts in species that have undergone intense artificial selection could help provide insights into the role of DNA methylation in populations subject to natural selection. This reference methylome for high producing Holstein cows provides a resource to more fully evaluate such relationships between variation in DNA methylation and phenotypic variation.

Example 2: Genomics Regions Showing Differential Methylation Patterns

The data presented herein shows the discovery of 500 differentially methylated DNA regions (DMR) between high milk, fat, and protein yield cows and their control.

Table 2 describes the DMRs' chromosome, starting and ending nucleotide coordinates (UMD_3.1, http://www.ncbi.nlm.nih.gov/assembly/GCA_000003055.4), FDR p-value, the identification of nearby annotated features (Ensembl release 82), and distance from the feature.

These DMR are located within genomic regions associated with gene regulation and variation results in differential expression of genes that influence the production of milk, fat, and protein. DMR effects vary depending on their location and can include regulation of transcription, alternative splicing, and long-range (LR) gene regulation. The nature of a specific DMR (transcription, alternative splicing, long-range regulation, etc.) is not definitive due to the incomplete annotation of bovine genome.

The 500 DMR range in length from 295 to 3699 with an average of 1026 bp. The Ensembl identification (Ensembl release 82) of the nearest annotated feature (protein-coding, miRNA, misc RNA, pseudogene, rRNA, snRNA, snoRNA) is provided for DMR that are located within a gene (intragenic), ≤100 kb upstream of a gene, ≤100 kb downstream of a gene, or LR elements (>100 kb from an annotated feature).

FIGS. 6-12 show selected DMR demonstrating the different relationships of DMR with annotated features. These data identify annotated features in close proximity to the DMR, features in the broader region (1 Mb), and the DNA methylation levels of high milk, fat, and protein yield cows compared to DNA methylation levels of controls.

TABLE 2

Description of each differentially methylated region (DMR) including chromosome (Chr), location, length, FDR p-value, type relative to nearest feature (Long range (LR); Downstreatm of gene (DS); Intragenic (IG); Upstream of gene (US)), Gene ID of nearest feature, feature name, feature type (non-coding (NC); snRNA, protein coding (PC), rRNA, processed pseudogene (PPG); pseudogene (PG); microRNA), and distance from feature

| Chr | DMR ID | starting nucleotide | ending nucleotide | DMR Length | FDR p-value | DMR type relative to nearest feature | Ensembl Gene ID of nearest feature | Feature Name | Feature type | DMR Distance from feature |
|---|---|---|---|---|---|---|---|---|---|---|
| 1 | 1 | 2650808 | 2651405 | 597 | 0.047 | LR | | | NC | |
| 1 | 2 | 8989523 | 8990173 | 650 | 0.023 | DS | ENSBTAG00000045024 | U6 | snRNA | 72612 |
| 1 | 3 | 15923286 | 15924699 | 1413 | 0.044 | LR | | | NC | |
| 1 | 4 | 18036256 | 18038006 | 1750 | 0.004 | US | ENSBTAG00000000597 | TMPRSS15 | PC | 20703 |
| 1 | 5 | 21178661 | 21180207 | 1546 | 0.004 | LR | | | NC | |
| 1 | 6 | 23257805 | 23259012 | 1207 | 0.025 | LR | | | NC | |
| 1 | 7 | 30023413 | 30024660 | 1247 | 0.013 | LR | | | NC | |
| 1 | 8 | 36447296 | 36447765 | 469 | 0.014 | LR | | | NC | |
| 1 | 9 | 40606654 | 40607309 | 655 | 0.033 | US | ENSBTAG00000044111 | | PC | 1420 |
| 1 | 10 | 47742931 | 47744277 | 1346 | 0.003 | LR | | | NC | |
| 1 | 11 | 49344409 | 49346408 | 1999 | 0.013 | LR | | | NC | |
| 1 | 12 | 52015737 | 52016133 | 396 | 0.017 | LR | | | NC | |
| 1 | 13 | 76453746 | 76454637 | 891 | 0.042 | DS | ENSBTAG00000006945 | CCDC50 | PC | 90777 |
| 1 | 14 | 81389637 | 81390639 | 1002 | 0.000 | LR | | | NC | |
| 1 | 15 | 81967092 | 81967696 | 604 | 0.015 | US | ENSBTAG00000007666 | IGF2BP2 | PC | 24702 |
| 1 | 16 | 89889011 | 89889692 | 681 | 0.002 | LR | | | NC | |
| 1 | 17 | 90680480 | 90681763 | 1283 | 0.044 | LR | | | NC | |
| 1 | 18 | 91574017 | 91575753 | 1736 | 0.041 | LR | | | NC | |
| 1 | 19 | 103923212 | 103924542 | 1330 | 0.022 | LR | | | NC | |
| 1 | 20 | 105875152 | 105876185 | 1033 | 0.005 | US | ENSBTAG00000011051 | | PG | 25291 |
| 1 | 21 | 108409914 | 108410633 | 719 | 0.025 | IG | ENSBTAG00000014960 | IQCJ-SCHIP1 | PC | 43848.5 |
| 1 | 22 | 113145236 | 113146730 | 1494 | 0.044 | US | ENSBTAG00000042550 | U6atac | snRNA | 7291 |
| 1 | 23 | 117951653 | 117952559 | 906 | 0.018 | US | ENSBTAG00000021703 | MED12L | PC | 34190 |
| 1 | 24 | 121424807 | 121426823 | 2016 | 0.021 | DS | ENSBTAG00000025146 | | PC | 3416 |
| 1 | 25 | 121617472 | 121619703 | 2231 | 0.004 | LR | | | NC | |
| 1 | 26 | 126382911 | 126385300 | 2389 | 0.026 | IG | ENSBTAG00000031178 | SLC9A9 | PC | 344016.5 |
| 1 | 27 | 127101647 | 127102216 | 569 | 0.044 | DS | ENSBTAG00000038111 | | PC | 26679 |
| 1 | 28 | 129889015 | 129890595 | 1580 | 0.031 | LR | | | NC | |
| 1 | 29 | 129908827 | 129909608 | 781 | 0.002 | LR | | | NC | |
| 1 | 30 | 130007044 | 130008350 | 1306 | 0.001 | US | ENSBTAG00000044978 | SNORD112 | snoRNA | 24531 |
| 1 | 31 | 142750141 | 142751044 | 903 | 0.029 | LR | | | NC | |
| 1 | 32 | 148995596 | 148996758 | 1162 | 0.027 | US | ENSBTAG00000044270 | bta-mir-2285a | miRNA | 87426 |
| 2 | 33 | 1859382 | 1860254 | 872 | 0.008 | IG | ENSBTAG00000000941 | PLEKHB2 | PC | 9711 |
| 2 | 34 | 7345944 | 7346755 | 811 | 0.025 | IG | ENSBTAG00000021466 | COL3A1 | PC | 10587.5 |
| 2 | 35 | 15008210 | 15009086 | 876 | 0.003 | US | ENSBTAG00000009257 | CERKL | PC | 17139 |
| 2 | 36 | 25054779 | 25055548 | 769 | 0.023 | IG | ENSBTAG00000007683 | DCAF17 | PC | 15216.5 |
| 2 | 37 | 28377660 | 28378906 | 1246 | 0.005 | DS | ENSBTAG00000003164 | B3GALT1 | PC | 21849 |
| 2 | 38 | 33344107 | 33345596 | 1489 | 0.016 | DS | ENSBTAG00000045366 | 7SK | RNA | 30735 |
| 2 | 39 | 48683607 | 48684638 | 1031 | 0.025 | LR | | | NC | |
| 2 | 40 | 50093023 | 50094234 | 1211 | 0.008 | LR | | | NC | |
| 2 | 41 | 50380428 | 50380988 | 560 | 0.000 | LR | | | NC | |
| 2 | 42 | 53148978 | 53150950 | 1972 | 0.008 | IG | ENSBTAG00000032289 | ARHGAP15 | PC | 582874 |
| 2 | 43 | 59574063 | 59575161 | 1098 | 0.015 | DS | ENSBTAG00000039437 | | PC | 79123 |
| 2 | 44 | 61012371 | 61013415 | 1044 | 0.021 | LR | | | NC | |
| 2 | 45 | 64339917 | 64340675 | 758 | 0.033 | LR | | | NC | |
| 2 | 46 | 75485084 | 75486163 | 1079 | 0.002 | LR | | | NC | |
| 2 | 47 | 78483589 | 78484320 | 731 | 0.029 | LR | | | NC | |
| 2 | 48 | 81570490 | 81571475 | 985 | 0.047 | US | ENSBTAG00000047783 | | PC | 67896 |
| 2 | 49 | 85024152 | 85025015 | 863 | 0.005 | IG | ENSBTAG00000016784 | DNAH7 | PC | 3474.5 |
| 2 | 50 | 91455806 | 91456799 | 993 | 0.016 | IG | ENSBTAG00000006420 | BMPR2 | PC | 60955.5 |
| 2 | 51 | 93884284 | 93885630 | 1346 | 0.043 | IG | ENSBTAG00000010293 | PARD3B | PC | 26604 |
| 2 | 52 | 121335843 | 121336299 | 456 | 0.032 | US | ENSBTAG00000020671 | TRIM62 | PC | 11562 |
| 3 | 53 | 6657747 | 6659074 | 1327 | 0.006 | IG | ENSBTAG00000005976 | HSD17B7 | PC | 656.5 |
| 3 | 54 | 11903752 | 11906506 | 2754 | 0.000 | IG | ENSBTAG00000026180 | | PC | 1865 |
| 3 | 55 | 23258398 | 23259165 | 767 | 0.034 | US | ENSBTAG00000007909 | NOTCH2 | PC | 47992 |
| 3 | 56 | 23380488 | 23381804 | 1316 | 0.048 | US | ENSBTAG00000007909 | NOTCH2 | PC | 73989 |
| 3 | 57 | 24040903 | 24042363 | 1460 | 0.047 | US | ENSBTAG00000005064 | WARS2 | PC | 63296 |
| 3 | 58 | 27865977 | 27867126 | 1149 | 0.017 | US | ENSBTAG00000005788 | VANGL1 | PC | 81984 |
| 3 | 59 | 29216930 | 29218124 | 1194 | 0.041 | LR | | | NC | |
| 3 | 60 | 54727832 | 54728827 | 995 | 0.014 | DS | ENSBTAG00000031186 | | PC | 30461 |
| 3 | 61 | 58380122 | 58380631 | 509 | 0.028 | DS | ENSBTAG00000047579 | | PPG | 47503 |
| 3 | 62 | 59009544 | 59010178 | 634 | 0.037 | US | ENSBTAG00000013851 | BCL10 | PC | 586 |
| 3 | 63 | 73492228 | 73493223 | 995 | 0.044 | LR | | | NC | |
| 3 | 64 | 79976887 | 79977706 | 673 | 0.029 | DS | ENSBTAG00000005910 | LEPR | PC | 94129 |
| 3 | 65 | 88338497 | 88339718 | 1221 | 0.021 | US | ENSBTAG00000007810 | | PG | 73748 |
| 3 | 66 | 88860377 | 88862690 | 2313 | 0.047 | LR | | | NC | |
| 3 | 67 | 90769181 | 90771019 | 1838 | 0.029 | LR | | | NC | |
| 3 | 68 | 93635184 | 93635865 | 681 | 0.026 | US | ENSBTAG00000014649 | CPT2 | PC | 9750 |
| 3 | 69 | 97092303 | 97093064 | 761 | 0.021 | LR | | | NC | |

TABLE 2-continued

Description of each differentially methylated region (DMR) including chromosome (Chr), location, length, FDR p-value, type relative to nearest feature (Long range (LR); Downstreatm of gene (DS); Intragenic (IG); Upstream of gene (US)), Gene ID of nearest feature, feature name, feature type (non-coding (NC); snRNA, protein coding (PC), rRNA, processed pseudogene (PPG); pseudogene (PG); microRNA), and distance from feature

| Chr | DMR ID | starting nucleotide | ending nucleotide | DMR Length | FDR p-value | DMR type relative to nearest feature | Ensembl Gene ID of nearest feature | Feature Name | Feature type | DMR Distance from feature |
|---|---|---|---|---|---|---|---|---|---|---|
| 3 | 70 | 105779155 | 105780912 | 1757 | 0.043 | IG | ENSBTAG00000001629 | SCMH1 | PC | 119615.5 |
| 3 | 71 | 108561195 | 108561971 | 776 | 0.030 | IG | ENSBTAG00000007299 | SF3A3 | PC | 1842 |
| 4 | 72 | 4315776 | 4316696 | 920 | 0.000 | LR | | | NC | |
| 4 | 73 | 8489373 | 8490559 | 1186 | 0.006 | US | ENSBTAG00000002107 | FZD1 | PC | 117 |
| 4 | 74 | 17938786 | 17939743 | 957 | 0.019 | LR | | | NC | |
| 4 | 75 | 19375274 | 19375927 | 653 | 0.004 | DS | ENSBTAG00000007680 | THSD7A | PC | 74729 |
| 4 | 76 | 19766014 | 19766763 | 749 | 0.015 | US | ENSBTAG00000007680 | THSD7A | PC | 38419 |
| 4 | 77 | 26066189 | 26066995 | 806 | 0.010 | DS | ENSBTAG00000042327 | U6 | snRNA | 31360 |
| 4 | 78 | 27486779 | 27488756 | 1977 | 0.034 | LR | | | NC | |
| 4 | 79 | 30562442 | 30563668 | 1226 | 0.031 | IG | ENSBTAG00000013078 | DNAH11 | PC | 142546 |
| 4 | 80 | 32151324 | 32152576 | 1252 | 0.039 | IG | ENSBTAG00000019406 | IGF2BP3 | PC | 70438 |
| 4 | 81 | 48233996 | 48235256 | 1260 | 0.035 | US | ENSBTAG00000020848 | PIK3CG | PC | 32319 |
| 4 | 82 | 49759636 | 49761026 | 1390 | 0.006 | US | ENSBTAG00000045095 | | miRNA | 281 |
| 4 | 83 | 56225987 | 56226552 | 565 | 0.042 | US | ENSBTAG00000013050 | ZNF277 | PC | 97322 |
| 4 | 84 | 57652648 | 57653519 | 871 | 0.013 | IG | ENSBTAG00000004398 | IMMP2L | PC | 525346.5 |
| 4 | 85 | 60546352 | 60547310 | 958 | 0.050 | IG | ENSBTAG00000003490 | ELMO1 | PC | 178392 |
| 4 | 86 | 64532285 | 64533069 | 784 | 0.045 | LR | | | NC | |
| 4 | 87 | 71123011 | 71123763 | 752 | 0.050 | US | ENSBTAG00000019445 | C7orf31 | PC | 15548 |
| 4 | 88 | 72610057 | 72611081 | 1024 | 0.002 | US | ENSBTAG00000024334 | | PPG | 35189 |
| 4 | 89 | 72903500 | 72904244 | 744 | 0.031 | US | ENSBTAG00000043385 | U6 | snRNA | 38401 |
| 4 | 90 | 79219030 | 79219677 | 647 | 0.013 | US | ENSBTAG00000027525 | | PG | 35472 |
| 4 | 91 | 79904055 | 79905689 | 1634 | 0.045 | US | ENSBTAG00000002912 | INHBA | PC | 80565 |
| 4 | 92 | 82426875 | 82427583 | 708 | 0.026 | IG | ENSBTAG00000013648 | POU6F2 | PC | 68071 |
| 4 | 93 | 86388901 | 86390015 | 1114 | 0.025 | IG | ENSBTAG00000002938 | CPED1 | PC | 139285 |
| 4 | 94 | 86454231 | 86455874 | 1643 | 0.005 | IG | ENSBTAG00000002938 | CPED1 | PC | 204879.5 |
| 4 | 95 | 101059413 | 101060658 | 1245 | 0.026 | LR | | | NC | |
| 4 | 96 | 111188291 | 111188740 | 449 | 0.047 | US | ENSBTAG00000000719 | | PC | 31311 |
| 4 | 97 | 116418944 | 116419632 | 688 | 0.002 | LR | | | NC | |
| 4 | 98 | 117710564 | 117711208 | 644 | 0.023 | IG | ENSBTAG00000021941 | DPP6 | PC | 155345 |
| 5 | 99 | 859820 | 860962 | 1142 | 0.029 | US | ENSBTAG00000019425 | TSPAN8 | PC | 2431 |
| 5 | 100 | 6973428 | 6974527 | 1099 | 0.025 | LR | | | NC | |
| 5 | 101 | 8828654 | 8829341 | 687 | 0.044 | US | ENSBTAG00000034693 | SYT1 | PC | 6760 |
| 5 | 102 | 8956835 | 8957433 | 598 | 0.028 | IG | ENSBTAG00000034693 | SYT1 | PC | 121033 |
| 5 | 103 | 11309127 | 11310405 | 1278 | 0.025 | LR | | | NC | |
| 5 | 104 | 14330849 | 14331622 | 773 | 0.025 | LR | | | NC | |
| 5 | 105 | 19735815 | 19737197 | 1382 | 0.026 | US | ENSBTAG00000009552 | ATP2B1 | PC | 66022 |
| 5 | 106 | 27936330 | 27937172 | 842 | 0.002 | DS | ENSBTAG00000000510 | ATG101 | PC | 25063 |
| 5 | 107 | 35237478 | 35238328 | 850 | 0.008 | US | ENSBTAG00000026249 | | PC | 62632 |
| 5 | 108 | 38881307 | 38882132 | 825 | 0.001 | LR | | | NC | |
| 5 | 109 | 40600473 | 40600768 | 295 | 0.023 | US | ENSBTAG00000026792 | | PC | 2886 |
| 5 | 110 | 43432500 | 43433449 | 949 | 0.002 | IG | ENSBTAG00000003748 | CNOT2 | PC | 61187.5 |
| 5 | 111 | 44118546 | 44119562 | 1016 | 0.041 | US | ENSBTAG00000019156 | CCT2 | PC | 2307 |
| 5 | 112 | 47387026 | 47387870 | 844 | 0.048 | LR | | | NC | |
| 5 | 113 | 60885721 | 60886735 | 1014 | 0.033 | IG | ENSBTAG00000001509 | ELK3 | PC | 62988 |
| 5 | 114 | 61969453 | 61970508 | 1055 | 0.035 | US | ENSBTAG00000038463 | bta-mir-1251 | miRNA | 72635 |
| 5 | 115 | 67594927 | 67595750 | 823 | 0.007 | US | ENSBTAG00000006010 | STAB2 | PC | 16697 |
| 5 | 116 | 69978482 | 69979156 | 674 | 0.006 | US | ENSBTAG00000011913 | CKAP4 | PC | 976 |
| 5 | 117 | 71704532 | 71705925 | 1393 | 0.002 | IG | ENSBTAG00000020636 | SYN3 | PC | 221489.5 |
| 5 | 118 | 72710869 | 72711749 | 880 | 0.031 | IG | ENSBTAG00000021953 | LARGE | PC | 58086 |
| 5 | 119 | 73148352 | 73149055 | 703 | 0.041 | LR | | | NC | |
| 5 | 120 | 73799853 | 73800910 | 860 | 0.000 | US | ENSBTAG00000010533 | HMGXB4 | PC | 70940 |
| 5 | 121 | 74864486 | 74865307 | 821 | 0.016 | DS | ENSBTAG00000039524 | | PC | 10647 |
| 5 | 122 | 75806125 | 75807426 | 1301 | 0.000 | IG | ENSBTAG00000030652 | TEX33 | PC | 1993.5 |
| 5 | 123 | 82469118 | 82469931 | 813 | 0.033 | US | ENSBTAG00000006372 | KLHL42 | PC | 417 |
| 5 | 124 | 94363478 | 94365255 | 1777 | 0.007 | IG | ENSBTAG00000023487 | COX6B1 | PC | 580.5 |
| 5 | 124 | 94363478 | 94365255 | 1777 | 0.007 | IG | ENSBTAG00000022167 | DERA | PC | 69980.5 |
| 5 | 125 | 94915414 | 94916363 | 949 | 0.030 | US | ENSBTAG00000026256 | PTPRO | PC | 33996 |
| 5 | 126 | 96484401 | 96484932 | 531 | 0.044 | IG | ENSBTAG00000000219 | GRIN2B | PC | 75862.5 |
| 5 | 127 | 101439094 | 101441030 | 1936 | 0.041 | IG | ENSBTAG00000018207 | M6PR | PC | 185 |
| 5 | 128 | 105155087 | 105156089 | 1002 | 0.037 | IG | ENSBTAG00000010223 | NTF3 | PC | 62136 |
| 6 | 129 | 8543483 | 8545058 | 1575 | 0.030 | LR | | | NC | |
| 6 | 130 | 20009756 | 20010231 | 475 | 0.013 | US | ENSBTAG00000047891 | | PC | 81135 |
| 6 | 131 | 20487933 | 20488939 | 1006 | 0.001 | IG | ENSBTAG00000006686 | NPNT | PC | 41523 |
| 6 | 132 | 24750368 | 24751958 | 1590 | 0.046 | US | ENSBTAG00000016005 | PPP3CA | PC | 60724 |
| 6 | 133 | 38449679 | 38451033 | 1354 | 0.043 | DS | ENSBTAG00000045804 | | miRNA | 90546 |
| 6 | 134 | 43572931 | 43573825 | 894 | 0.001 | US | ENSBTAG00000004653 | ADGRA3 | PC | 41511 |
| 6 | 135 | 47659212 | 47661245 | 2033 | 0.003 | IG | ENSBTAG00000033214 | TBC1D19 | PC | 90166.5 |
| 6 | 136 | 52520434 | 52521120 | 686 | 0.014 | LR | | | NC | |
| 6 | 137 | 57688011 | 57688593 | 582 | 0.050 | LR | | | NC | |

TABLE 2-continued

Description of each differentially methylated region (DMR) including chromosome (Chr), location, length, FDR p-value, type relative to nearest feature (Long range (LR); Downstreatm of gene (DS); Intragenic (IG); Upstream of gene (US)), Gene ID of nearest feature, feature name, feature type (non-coding (NC); snRNA, protein coding (PC), rRNA, processed pseudogene (PPG); pseudogene (PG); microRNA), and distance from feature

| Chr | DMR ID | starting nucleotide | ending nucleotide | DMR Length | FDR p-value | DMR type relative to nearest feature | Ensembl Gene ID of nearest feature | Feature Name | Feature type | DMR Distance from feature |
|---|---|---|---|---|---|---|---|---|---|---|
| 6 | 138 | 74814402 | 74815338 | 936 | 0.007 | LR | | | NC | |
| 6 | 139 | 80743118 | 80743908 | 790 | 0.019 | LR | | | NC | |
| 6 | 140 | 82398025 | 82399840 | 1815 | 0.008 | LR | | | NC | |
| 6 | 141 | 91568328 | 91569155 | 827 | 0.015 | US | ENSBTAG00000015919 | PARM1 | PC | 27967 |
| 6 | 142 | 93048386 | 93049655 | 1269 | 0.001 | IG | ENSBTAG00000012157 | CCDC158 | PC | 9317.5 |
| 6 | 143 | 94295485 | 94296253 | 768 | 0.039 | US | ENSBTAG00000018360 | MRPL1 | PC | 41671 |
| 6 | 144 | 105632133 | 105632890 | 757 | 0.004 | LR | | | NC | |
| 7 | 145 | 2031963 | 2032676 | 713 | 0.044 | IG | ENSBTAG00000014665 | ADAMTS2 | PC | 75967.5 |
| 7 | 146 | 2661698 | 2663035 | 1337 | 0.014 | US | ENSBTAG00000040028 | | PC | 43216 |
| 7 | 147 | 15423354 | 15424363 | 1009 | 0.033 | IG | ENSBTAG00000046265 | ZFP62 | PC | 18049.5 |
| 7 | 148 | 18538622 | 18539579 | 957 | 0.020 | DS | ENSBTAG00000047533 | | PG | 34395 |
| 7 | 149 | 29186811 | 29187206 | 395 | 0.037 | US | ENSBTAG00000043765 | U2 | snRNA | 11925 |
| 7 | 150 | 29289973 | 29290886 | 913 | 0.041 | LR | | | NC | |
| 7 | 151 | 30881320 | 30882591 | 1271 | 0.026 | LR | | | NC | |
| 7 | 152 | 33408261 | 33409584 | 1323 | 0.022 | US | ENSBTAG00000005779 | FTMT | PC | 95171 |
| 7 | 153 | 38452127 | 38453623 | 1496 | 0.001 | LR | | | NC | |
| 7 | 154 | 39473981 | 39474579 | 598 | 0.011 | IG | ENSBTAG00000017451 | TSPAN17 | PC | 1663 |
| 7 | 155 | 47014698 | 47015312 | 614 | 0.013 | LR | | | NC | |
| 7 | 156 | 48901817 | 48902681 | 864 | 0.048 | IG | ENSBTAG00000018287 | SLC25A48 | PC | 44015 |
| 7 | 157 | 49801240 | 49801985 | 745 | 0.009 | LR | | | NC | |
| 7 | 158 | 49840302 | 49841129 | 827 | 0.049 | LR | | | NC | |
| 7 | 159 | 56730876 | 56731930 | 1054 | 0.001 | LR | | | NC | |
| 7 | 160 | 58334961 | 58335870 | 909 | 0.037 | LR | | | NC | |
| 7 | 161 | 59583712 | 59584616 | 904 | 0.016 | US | ENSBTAG00000042815 | U6 | snRNA | 24927 |
| 7 | 162 | 60133913 | 60135221 | 1308 | 0.035 | US | ENSBTAG00000001862 | PPP2R2B | PC | 34501 |
| 7 | 163 | 69396412 | 69397542 | 1130 | 0.002 | LR | | | NC | |
| 7 | 164 | 76699247 | 76700626 | 1379 | 0.016 | LR | | | NC | |
| 7 | 165 | 87231129 | 87231783 | 654 | 0.000 | LR | | | NC | |
| 7 | 166 | 89046431 | 89047606 | 1175 | 0.049 | US | ENSBTAG00000028668 | 5S_rRNA | rRNA | 92705 |
| 8 | 167 | 6678156 | 6680504 | 2348 | 0.025 | IG | ENSBTAG00000025942 | HPGD | PC | 1216 |
| 8 | 168 | 17766046 | 17767193 | 1147 | 0.024 | US | ENSBTAG00000043403 | U6 | snRNA | 14279 |
| 8 | 169 | 26336432 | 26336943 | 511 | 0.029 | LR | | | NC | |
| 8 | 170 | 27493170 | 27493967 | 797 | 0.019 | LR | | | NC | |
| 8 | 171 | 28195694 | 28196437 | 743 | 0.041 | LR | | | NC | |
| 8 | 172 | 29791778 | 29792495 | 717 | 0.049 | US | ENSBTAG00000047378 | | miRNA | 58258 |
| 8 | 173 | 30402201 | 30404283 | 2082 | 0.025 | LR | | | NC | |
| 8 | 174 | 32980920 | 32981763 | 843 | 0.013 | LR | | | NC | |
| 8 | 175 | 39366572 | 39367858 | 1286 | 0.003 | DS | ENSBTAG00000043615 | U6 | snRNA | 9857 |
| 8 | 176 | 41822526 | 41824045 | 1519 | 0.029 | LR | | | NC | |
| 8 | 177 | 46039906 | 46040646 | 740 | 0.013 | US | ENSBTAG00000008877 | APBA1 | PC | 90380 |
| 8 | 178 | 49977429 | 49978917 | 1488 | 0.049 | LR | | | NC | |
| 8 | 179 | 51613811 | 51614424 | 613 | 0.019 | DS | ENSBTAG00000046039 | | PG | 191 |
| 8 | 180 | 54550439 | 54551205 | 766 | 0.021 | LR | | | NC | |
| 8 | 181 | 77125146 | 77125823 | 677 | 0.025 | IG | ENSBTAG00000008537 | FAM219A | PC | 39680.5 |
| 8 | 181 | 77125146 | 77125823 | 677 | 0.025 | IG | ENSBTAG00000005495 | | PC | 74949.5 |
| 8 | 182 | 79355950 | 79357013 | 1063 | 0.025 | IG | ENSBTAG00000010647 | NTRK2 | PC | 20193.5 |
| 8 | 183 | 97127081 | 97127819 | 803 | 0.006 | IG | ENSBTAG00000046079 | | PPG | 10.5 |
| 8 | 184 | 99219752 | 99221235 | 1483 | 0.014 | LR | | | NC | |
| 8 | 185 | 103665920 | 103666522 | 602 | 0.005 | DS | ENSBTAG00000019275 | INIP | PC | 2610 |
| 8 | 186 | 103870084 | 103870526 | 442 | 0.043 | DS | ENSBTAG00000018481 | | PC | 36075 |
| 8 | 187 | 108878567 | 108880259 | 1692 | 0.010 | LR | | | NC | |
| 8 | 188 | 111956916 | 111957669 | 753 | 0.013 | IG | ENSBTAG00000013706 | MEGF9 | PC | 37977.5 |
| 9 | 189 | 6643712 | 6644276 | 564 | 0.026 | LR | | | NC | |
| 9 | 190 | 9812829 | 9813424 | 595 | 0.042 | US | ENSBTAG00000002171 | FAM135A | PC | 2663 |
| 9 | 191 | 11074028 | 11074830 | 802 | 0.025 | LR | | | NC | |
| 9 | 192 | 11899078 | 11900166 | 1088 | 0.035 | US | ENSBTAG00000020238 | RIMS1 | PC | 218582 |
| 9 | 193 | 13204265 | 13204949 | 684 | 0.031 | IG | ENSBTAG00000016839 | MTO1 | PC | 15439 |
| 9 | 194 | 14571758 | 14572813 | 1055 | 0.008 | LR | | | NC | |
| 9 | 195 | 23739563 | 23741013 | 1450 | 0.013 | DS | ENSBTAG00000009355 | SNAP91 | PC | 5487 |
| 9 | 196 | 24932716 | 24933797 | 1081 | 0.048 | LR | | | NC | |
| 9 | 197 | 29171200 | 29171896 | 696 | 0.041 | US | ENSBTAG00000012946 | HSF2 | PC | 9594 |
| 9 | 198 | 30740873 | 30741470 | 597 | 0.040 | LR | | | NC | |
| 9 | 199 | 35572366 | 35572761 | 395 | 0.025 | LR | | | NC | |
| 9 | 200 | 44256617 | 44257352 | 735 | 0.014 | US | ENSBTAG00000025108 | | PG | 55752 |
| 9 | 201 | 50219921 | 50220915 | 994 | 0.013 | IG | ENSBTAG00000002294 | SIM1 | PC | 59721 |
| 9 | 202 | 52702945 | 52703530 | 585 | 0.035 | LR | | | NC | |
| 9 | 203 | 58335507 | 58336421 | 914 | 0.002 | LR | | | NC | |
| 9 | 204 | 60727369 | 60728558 | 1189 | 0.030 | LR | | | NC | |
| 9 | 205 | 64387065 | 64388125 | 1060 | 0.002 | LR | | | NC | |

TABLE 2-continued

Description of each differentially methylated region (DMR) including chromosome (Chr), location, length, FDR p-value, type relative to nearest feature (Long range (LR); Downstreatm of gene (DS); Intragenic (IG); Upstream of gene (US)), Gene ID of nearest feature, feature name, feature type (non-coding (NC); snRNA, protein coding (PC), rRNA, processed pseudogene (PPG); pseudogene (PG); microRNA), and distance from feature

| Chr | DMR ID | starting nucleotide | ending nucleotide | DMR Length | FDR p-value | DMR type relative to nearest feature | Ensembl Gene ID of nearest feature | Feature Name | Feature type | DMR Distance from feature |
|---|---|---|---|---|---|---|---|---|---|---|
| 9 | 206 | 74353225 | 74355044 | 1819 | 0.048 | IG | ENSBTAG00000017958 | AHI1 | PC | 189925.5 |
| 9 | 207 | 82541646 | 82542758 | 1112 | 0.002 | DS | ENSBTAG00000009795 | SF3B5 | PC | 6768 |
| 9 | 208 | 82562944 | 82564362 | 1418 | 0.013 | US | ENSBTAG00000009795 | SF3B5 | PC | 12746 |
| 9 | 209 | 83404211 | 83405215 | 1004 | 0.043 | LR | | | NC | |
| 9 | 210 | 87284395 | 87285475 | 1080 | 0.004 | LR | | | NC | |
| 9 | 211 | 89590447 | 89591452 | 1005 | 0.013 | IG | ENSBTAG00000014790 | ZBTB2 | PC | 13013.5 |
| 9 | 212 | 90554194 | 90555238 | 1044 | 0.021 | IG | ENSBTAG00000009362 | SYNE1 | PC | 115630 |
| 9 | 213 | 90658909 | 90659903 | 994 | 0.003 | IG | ENSBTAG00000009362 | SYNE1 | PC | 10940 |
| 9 | 214 | 97071108 | 97072175 | 1067 | 0.015 | LR | | | NC | |
| 10 | 215 | 3779654 | 3780298 | 644 | 0.049 | LR | | | NC | |
| 10 | 216 | 8923856 | 8924933 | 1077 | 0.027 | LR | | | NC | |
| 10 | 217 | 9326134 | 9326588 | 454 | 0.049 | US | ENSBTAG00000005016 | AP3B1 | PC | 25567 |
| 10 | 218 | 9890553 | 9891322 | 769 | 0.013 | IG | ENSBTAG00000008341 | ARSB | PC | 83981.5 |
| 10 | 219 | 11997271 | 11998141 | 870 | 0.021 | DS | ENSBTAG00000039658 | PDCD7 | PC | 23307 |
| 10 | 220 | 12910200 | 12911062 | 862 | 0.045 | LR | | | NC | |
| 10 | 221 | 18250198 | 18251170 | 972 | 0.029 | LR | | | NC | |
| 10 | 222 | 27733514 | 27734596 | 1082 | 0.004 | US | ENSBTAG00000046061 | | PC | 44010 |
| 10 | 223 | 30784702 | 30785419 | 717 | 0.003 | LR | | | NC | |
| 10 | 224 | 43035935 | 43036811 | 876 | 0.031 | DS | ENSBTAG00000005547 | VCPKMT | PC | 52567 |
| 10 | 225 | 50908674 | 50909425 | 751 | 0.029 | IG | ENSBTAG00000014699 | FAM81A | PC | 22363.5 |
| 10 | 226 | 65723856 | 65724482 | 626 | 0.010 | US | ENSBTAG00000047170 | | PC | 22708 |
| 10 | 227 | 70442907 | 70443888 | 981 | 0.019 | US | ENSBTAG00000036635 | 5S_rRNA | rRNA | 705 |
| 10 | 228 | 73685249 | 73686329 | 1080 | 0.013 | US | ENSBTAG00000003276 | PRKCH | PC | 8339 |
| 10 | 229 | 76480829 | 76481558 | 729 | 0.040 | IG | ENSBTAG00000025450 | SYNE2 | PC | 119170.5 |
| 10 | 230 | 81787036 | 81787536 | 500 | 0.003 | IG | ENSBTAG00000003857 | SUSD6 | PC | 35682 |
| 10 | 231 | 85407920 | 85408469 | 549 | 0.019 | US | ENSBTAG00000010270 | | PC | 23341 |
| 10 | 232 | 85767617 | 85768879 | 1262 | 0.007 | US | ENSBTAG00000018467 | CCDC176 | PC | 8006 |
| 10 | 233 | 90937169 | 90937998 | 829 | 0.000 | LR | | | NC | |
| 10 | 234 | 94101826 | 94102687 | 861 | 0.031 | DS | ENSBTAG00000045343 | 5S_rRNA | rRNA | 51062 |
| 10 | 235 | 97734259 | 97735264 | 1005 | 0.045 | LR | | | NC | |
| 10 | 236 | 100548979 | 100549883 | 904 | 0.006 | LR | | | NC | |
| 11 | 237 | 15073492 | 15074079 | 587 | 0.040 | IG | ENSBTAG00000027932 | BIRC6 | PC | 93854.5 |
| 11 | 238 | 23496803 | 23497558 | 755 | 0.001 | LR | | | NC | |
| 11 | 239 | 31895527 | 31897389 | 1862 | 0.001 | LR | | | NC | |
| 11 | 240 | 33036706 | 33037407 | 660 | 0.002 | LR | | | NC | |
| 11 | 241 | 35584689 | 35585743 | 1054 | 0.017 | LR | | | NC | |
| 11 | 242 | 36618691 | 36619755 | 1064 | 0.008 | US | ENSBTAG00000024019 | | PC | 51175 |
| 11 | 243 | 40939206 | 40939886 | 680 | 0.004 | LR | | | NC | |
| 11 | 244 | 41462380 | 41464011 | 1631 | 0.045 | LR | | | NC | |
| 11 | 245 | 43011791 | 43012786 | 995 | 0.004 | DS | ENSBTAG00000016534 | BCL11A | PC | 59191 |
| 11 | 246 | 45893330 | 45894723 | 1393 | 0.040 | US | ENSBTAG00000015205 | NCK2 | PC | 63364 |
| 11 | 247 | 46139229 | 46140793 | 1564 | 0.004 | US | ENSBTAG00000007895 | SLC20A1 | PC | 77923 |
| 11 | 248 | 47050864 | 47051813 | 949 | 0.007 | IG | ENSBTAG00000047029 | | PC | 196.5 |
| 11 | 249 | 47083085 | 47083474 | 389 | 0.002 | US | ENSBTAG00000003408 | | PC | 20961 |
| 11 | 250 | 55068515 | 55069894 | 1379 | 0.046 | IG | ENSBTAG00000031669 | | PC | 837257.5 |
| 11 | 251 | 58586939 | 58588898 | 1959 | 0.014 | LR | | | NC | |
| 11 | 252 | 69881439 | 69882193 | 754 | 0.022 | LR | | | NC | |
| 11 | 253 | 76737823 | 76739417 | 1594 | 0.039 | LR | | | NC | |
| 11 | 254 | 77658692 | 77659393 | 701 | 0.046 | US | ENSBTAG00000030834 | | PC | 9781 |
| 11 | 255 | 82571008 | 82571711 | 703 | 0.048 | LR | | | NC | |
| 11 | 256 | 85784994 | 85785730 | 736 | 0.046 | LR | | | NC | |
| 11 | 257 | 97460388 | 97460973 | 585 | 0.000 | US | ENSBTAG00000010228 | LMX1B | PC | 14333 |
| 12 | 258 | 17942701 | 17943355 | 654 | 0.016 | US | ENSBTAG00000006759 | SUCLA2 | PC | 11768 |
| 12 | 259 | 18496476 | 18497097 | 621 | 0.044 | US | ENSBTAG00000017508 | CYSLTR2 | PC | 28383 |
| 12 | 260 | 30650584 | 30651104 | 520 | 0.046 | US | ENSBTAG00000045239 | SNORA70 | snoRNA | 63395 |
| 12 | 261 | 31139647 | 31141465 | 1818 | 0.039 | IG | ENSBTAG00000001094 | MTUS2 | PC | 155513 |
| 12 | 262 | 32353150 | 32354774 | 1624 | 0.018 | IG | ENSBTAG00000010690 | PDX1 | PC | 3265 |
| 12 | 263 | 35975471 | 35976823 | 1352 | 0.018 | IG | ENSBTAG00000003710 | XPO4 | PC | 17790 |
| 12 | 264 | 46661886 | 46663109 | 1223 | 0.031 | LR | | | NC | |
| 12 | 265 | 54297384 | 54298366 | 982 | 0.019 | LR | | | NC | |
| 12 | 266 | 64259051 | 64260173 | 1122 | 0.046 | LR | | | NC | |
| 12 | 267 | 64939332 | 64939990 | 658 | 0.001 | LR | | | NC | |
| 12 | 268 | 70026271 | 70026927 | 656 | 0.018 | IG | ENSBTAG00000032603 | | PC | 144921 |
| 12 | 269 | 73339506 | 73341745 | 2239 | 0.002 | LR | | | NC | |
| 12 | 270 | 76302873 | 76303290 | 417 | 0.004 | LR | | | NC | |
| 12 | 271 | 78039262 | 78039734 | 472 | 0.023 | US | ENSBTAG00000021345 | OXGR1 | PC | 24110 |
| 12 | 272 | 80263920 | 80264487 | 567 | 0.003 | US | ENSBTAG00000038268 | | PC | 19857 |
| 12 | 273 | 82449572 | 82451685 | 2113 | 0.041 | LR | | | NC | |
| 12 | 274 | 85117388 | 85117794 | 406 | 0.029 | LR | | | NC | |

TABLE 2-continued

Description of each differentially methylated region (DMR) including chromosome (Chr), location, length, FDR p-value, type relative to nearest feature (Long range (LR); Downstream of gene (DS); Intragenic (IG); Upstream of gene (US)), Gene ID of nearest feature, feature name, feature type (non-coding (NC); snRNA, protein coding (PC), rRNA, processed pseudogene (PPG); pseudogene (PG); microRNA), and distance from feature

| Chr | DMR ID | starting nucleotide | ending nucleotide | DMR Length | FDR p-value | DMR type relative to nearest feature | Ensembl Gene ID of nearest feature | Feature Name | Feature type | DMR Distance from feature |
|---|---|---|---|---|---|---|---|---|---|---|
| 13 | 275 | 4498816 | 4499670 | 854 | 0.045 | LR | | | NC | |
| 13 | 276 | 5124108 | 5125092 | 984 | 0.008 | LR | | | NC | |
| 13 | 277 | 8902709 | 8903143 | 434 | 0.041 | LR | | | NC | |
| 13 | 278 | 14088922 | 14089552 | 630 | 0.048 | LR | | | NC | |
| 13 | 279 | 17102782 | 17103450 | 668 | 0.035 | IG | ENSBTAG00000010664 | PRKCQ | PC | 9502 |
| 13 | 280 | 18281726 | 18282519 | 793 | 0.020 | IG | ENSBTAG00000012526 | APBB1IP | PC | 52605.5 |
| 13 | 281 | 34144808 | 34145621 | 813 | 0.013 | IG | ENSBTAG00000020053 | ZEB1 | PC | 116084.5 |
| 13 | 282 | 35688021 | 35688964 | 943 | 0.006 | DS | ENSBTAG00000010330 | | PC | 90593 |
| 13 | 283 | 35853158 | 35853958 | 800 | 0.008 | US | ENSBTAG00000010330 | | PC | 57589 |
| 13 | 284 | 38173622 | 38175474 | 1852 | 0.001 | DS | ENSBTAG00000021867 | BFSP1 | PC | 6848 |
| 13 | 285 | 38952024 | 38953086 | 1062 | 0.002 | IG | ENSBTAG00000008964 | DTD1 | PC | 43005 |
| 13 | 286 | 40406832 | 40407677 | 845 | 0.025 | IG | ENSBTAG00000014178 | RALGAPA2 | PC | 128134.5 |
| 13 | 287 | 43868618 | 43869384 | 766 | 0.025 | IG | ENSBTAG00000027419 | | PC | 4717 |
| 13 | 288 | 62123019 | 62123219 | 1200 | 0.006 | IG | ENSBTAG00000007932 | HCK | PC | 16362 |
| 13 | 289 | 62485129 | 62485940 | 811 | 0.030 | IG | ENSBTAG00000008348 | NOL4L | PC | 14156.5 |
| 13 | 290 | 63154822 | 63155695 | 873 | 0.013 | US | ENSBTAG00000019752 | | PC | 9611 |
| 13 | 291 | 76630206 | 76630982 | 776 | 0.010 | US | ENSBTAG00000013114 | ZMYND8 | PC | 5194 |
| 14 | 292 | 6980774 | 6981488 | 714 | 0.029 | LR | | | NC | |
| 14 | 293 | 13380011 | 13380470 | 459 | 0.013 | LR | | | NC | |
| 14 | 294 | 14748251 | 14749211 | 960 | 0.003 | LR | | | NC | |
| 14 | 295 | 27406130 | 27409484 | 3354 | 0.045 | LR | | | NC | |
| 14 | 296 | 28580800 | 28581487 | 687 | 0.023 | LR | | | NC | |
| 14 | 297 | 29510637 | 29511155 | 518 | 0.049 | LR | | | NC | |
| 14 | 298 | 34711877 | 34713166 | 1289 | 0.019 | IG | ENSBTAG00000022588 | C8orf34 | PC | 284942.5 |
| 14 | 299 | 47788062 | 47789446 | 1384 | 0.029 | IG | ENSBTAG00000043996 | SAMD12 | PC | 9158 |
| 14 | 300 | 57370784 | 57371388 | 604 | 0.041 | LR | | | NC | |
| 14 | 301 | 57907447 | 57908638 | 1191 | 0.019 | LR | | | NC | |
| 14 | 302 | 62365801 | 62366865 | 1064 | 0.014 | IG | ENSBTAG00000021887 | DPYS | PC | 38201 |
| 14 | 302 | 62365801 | 62366865 | 1064 | 0.014 | IG | ENSBTAG00000021240 | DCSTAMP | PC | 85328 |
| 14 | 303 | 63458120 | 63458896 | 776 | 0.029 | IG | ENSBTAG00000026242 | BAALC | PC | 75584 |
| 14 | 304 | 72632035 | 72633542 | 1507 | 0.013 | DS | ENSBTAG00000000199 | PDP1 | PC | 45052 |
| 14 | 305 | 75141948 | 75142689 | 741 | 0.001 | LR | | | NC | |
| 14 | 306 | 78988406 | 78988922 | 516 | 0.043 | US | ENSBTAG00000043511 | SNORA61 | snoRNA | 19827 |
| 14 | 307 | 79188808 | 79190450 | 1642 | 0.014 | LR | | | NC | |
| 14 | 308 | 79200093 | 79202068 | 2075 | 0.025 | US | ENSBTAG00000002851 | | PC | 94545 |
| 14 | 309 | 79212220 | 79214156 | 1936 | 0.026 | US | ENSBTAG00000002851 | | PC | 82557 |
| 14 | 310 | 79501005 | 79501655 | 650 | 0.003 | US | ENSBTAG00000032236 | | PC | 18978 |
| 15 | 311 | 7620895 | 7622126 | 1231 | 0.026 | US | ENSBTAG00000011227 | TRPC6 | PC | 30862 |
| 15 | 312 | 10307064 | 10309585 | 2521 | 0.020 | LR | | | NC | |
| 15 | 313 | 13378789 | 13379573 | 784 | 0.031 | LR | | | NC | |
| 15 | 314 | 23030664 | 23031345 | 681 | 0.049 | US | ENSBTAG00000015810 | PLET1 | PC | 40186 |
| 15 | 315 | 27564472 | 27565110 | 638 | 0.018 | LR | | | NC | |
| 15 | 316 | 41994601 | 41995928 | 1327 | 0.026 | LR | | | NC | |
| 15 | 317 | 42090537 | 42091525 | 988 | 0.011 | LR | | | NC | |
| 15 | 318 | 49953069 | 49954390 | 1321 | 0.001 | US | ENSBTAG00000035006 | | PC | 29317 |
| 15 | 319 | 50681217 | 50682160 | 943 | 0.030 | US | ENSBTAG00000039654 | | PG | 773 |
| 15 | 320 | 56817411 | 56817957 | 546 | 0.002 | DS | ENSBTAG00000001301 | LRRC32 | PC | 9135 |
| 15 | 321 | 56949485 | 56950898 | 1413 | 0.025 | US | ENSBTAG00000001537 | TSKU | PC | 10422 |
| 15 | 322 | 60563275 | 60563880 | 605 | 0.009 | LR | | | NC | |
| 16 | 323 | 10089479 | 10091569 | 2090 | 0.044 | LR | | | NC | |
| 16 | 324 | 14439290 | 14439741 | 451 | 0.048 | LR | | | NC | |
| 16 | 325 | 33756304 | 33756900 | 596 | 0.029 | LR | | | NC | |
| 16 | 326 | 37043439 | 37043774 | 335 | 0.040 | DS | ENSBTAG00000021211 | DPT | PC | 62859 |
| 16 | 327 | 40093808 | 40094705 | 897 | 0.041 | US | ENSBTAG00000014319 | DNM3 | PC | 24040 |
| 16 | 328 | 41305025 | 41306287 | 1262 | 0.009 | LR | | | NC | |
| 16 | 329 | 43614440 | 43615054 | 614 | 0.005 | LR | | | NC | |
| 16 | 330 | 44632003 | 44632546 | 543 | 0.045 | US | ENSBTAG00000011823 | CLSTN1 | PC | 777 |
| 16 | 331 | 49975905 | 49976923 | 1018 | 0.007 | LR | | | NC | |
| 16 | 332 | 50229126 | 50231169 | 2043 | 0.003 | LR | | | NC | |
| 16 | 333 | 52192386 | 52194258 | 1872 | 0.016 | US | ENSBTAG00000000212 | NADK | PC | 9454 |
| 16 | 334 | 56779163 | 56779840 | 677 | 0.043 | US | ENSBTAG00000004362 | SERPINC1 | PC | 44883 |
| 16 | 335 | 57121293 | 57122619 | 1326 | 0.034 | US | ENSBTAG00000038189 | GPR52 | PC | 87341 |
| 16 | 336 | 61204663 | 61205226 | 563 | 0.031 | IG | ENSBTAG00000015537 | RASAL2 | PC | 83866.5 |
| 16 | 337 | 65516011 | 65516792 | 781 | 0.019 | US | ENSBTAG00000011966 | LAMC1 | PC | 28705 |
| 16 | 338 | 77856105 | 77856837 | 732 | 0.000 | IG | ENSBTAG00000000070 | F13B | PC | 8330 |
| 16 | 339 | 78236168 | 78236875 | 707 | 0.023 | IG | ENSBTAG00000008944 | CRB1 | PC | 141763.5 |
| 16 | 340 | 78790537 | 78791890 | 1353 | 0.002 | IG | ENSBTAG00000013499 | LHX9 | PC | 6291.5 |
| 17 | 341 | 11597954 | 11599205 | 1251 | 0.008 | IG | ENSBTAG00000004167 | TTC29 | PC | 118642.5 |
| 17 | 342 | 18758755 | 18760167 | 1412 | 0.022 | IG | ENSBTAG00000015811 | | PC | 297 |

TABLE 2-continued

Description of each differentially methylated region (DMR) including chromosome (Chr), location, length, FDR p-value, type relative to nearest feature (Long range (LR); Downstreatm of gene (DS); Intragenic (IG); Upstream of gene (US)), Gene ID of nearest feature, feature name, feature type (non-coding (NC); snRNA, protein coding (PC), rRNA, processed pseudogene (PPG); pseudogene (PG); microRNA), and distance from feature

| Chr | DMR ID | starting nucleotide | ending nucleotide | DMR Length | FDR p-value | DMR type relative to nearest feature | Ensembl Gene ID of nearest feature | Feature Name | Feature type | DMR Distance from feature |
|---|---|---|---|---|---|---|---|---|---|---|
| 17 | 343 | 29614626 | 29615246 | 620 | 0.044 | LR | | | NC | |
| 17 | 344 | 34911465 | 34911929 | 464 | 0.044 | IG | ENSBTAG00000000125 | SPATA5 | PC | 234020 |
| 17 | 345 | 44064169 | 44065834 | 1665 | 0.031 | LR | | | NC | |
| 17 | 346 | 53937162 | 53937632 | 470 | 0.034 | DS | ENSBTAG00000039023 | ZNF664 | PC | 32063 |
| 17 | 347 | 67613340 | 67614059 | 719 | 0.029 | US | ENSBTAG00000000005 | ADRBK2 | PC | 54960 |
| 17 | 348 | 68596004 | 68596588 | 584 | 0.008 | IG | ENSBTAG00000031468 | | PC | 281 |
| 17 | 349 | 70286517 | 70287371 | 854 | 0.034 | IG | ENSBTAG00000004956 | CHEK2 | PC | 18303 |
| 17 | 350 | 71304138 | 71305285 | 1147 | 0.006 | IG | ENSBTAG00000013877 | HORMAD2 | PC | 21142.5 |
| 18 | 351 | 8726490 | 8727114 | 624 | 0.044 | IG | ENSBTAG00000003234 | HSD17B2 | PC | 90760 |
| 18 | 352 | 12415448 | 12416200 | 752 | 0.001 | US | ENSBTAG00000012446 | MTHFSD | PC | 92 |
| 18 | 353 | 23684116 | 23684938 | 822 | 0.039 | IG | ENSBTAG00000016407 | IRX6 | PC | 2928 |
| 18 | 354 | 24061068 | 24061702 | 634 | 0.045 | US | ENSBTAG00000001851 | | PC | 4707 |
| 18 | 355 | 33694408 | 33695487 | 1079 | 0.021 | LR | | | NC | |
| 18 | 356 | 50970695 | 50970991 | 296 | 0.020 | LR | | | NC | |
| 18 | 357 | 51143685 | 51144611 | 926 | 0.007 | IG | ENSBTAG00000005615 | CEACAM1 | PC | 5858 |
| 18 | 358 | 52570722 | 52572036 | 1314 | 0.046 | DS | ENSBTAG00000040209 | ZNF112 | PC | 10587 |
| 18 | 359 | 56565222 | 56567367 | 2145 | 0.008 | IG | ENSBTAG00000012205 | CPT1C | PC | 18542.5 |
| 18 | 360 | 61451973 | 61453166 | 1193 | 0.031 | LR | | | NC | |
| 18 | 361 | 62243354 | 62244165 | 811 | 0.003 | IG | ENSBTAG00000004725 | NLRP9 | PC | 1475.5 |
| 19 | 362 | 4635028 | 4636169 | 1141 | 0.040 | LR | | | NC | |
| 19 | 363 | 8634252 | 8635332 | 1080 | 0.028 | US | ENSBTAG00000004406 | MSI2 | PC | 16431 |
| 19 | 364 | 12040792 | 12041605 | 813 | 0.039 | US | ENSBTAG00000014278 | TBX2 | PC | 89381 |
| 19 | 365 | 14083295 | 14083969 | 674 | 0.041 | IG | ENSBTAG00000014677 | TADA2A | PC | 43150 |
| 19 | 366 | 19849240 | 19850781 | 1541 | 0.014 | IG | ENSBTAG00000024490 | | PC | 16285.5 |
| 19 | 366 | 19849240 | 19850781 | 1541 | 0.014 | IG | ENSBTAG00000006894 | NOS2 | PC | 106538.5 |
| 19 | 367 | 20227919 | 20228364 | 445 | 0.000 | IG | ENSBTAG00000014825 | NLK | PC | 50294.5 |
| 19 | 368 | 23591789 | 23592625 | 836 | 0.013 | US | ENSBTAG00000012302 | RTN4RL1 | PC | 31123 |
| 19 | 369 | 23691174 | 23691720 | 546 | 0.025 | IG | ENSBTAG00000000267 | SMG6 | PC | 167044 |
| 19 | 370 | 26085470 | 26086310 | 840 | 0.000 | US | ENSBTAG00000002981 | FAM64A | PC | 59461 |
| 19 | 371 | 26443728 | 26444654 | 926 | 0.002 | LR | | | NC | |
| 19 | 372 | 31168535 | 31169354 | 819 | 0.002 | IG | ENSBTAG00000022509 | DNAH9 | PC | 205426.5 |
| 19 | 373 | 32140181 | 32140996 | 815 | 0.025 | LR | | | NC | |
| 19 | 374 | 32687094 | 32687970 | 876 | 0.044 | US | ENSBTAG00000015294 | COX10 | PC | 8467 |
| 19 | 375 | 38225336 | 38226680 | 1344 | 0.034 | IG | ENSBTAG00000018803 | SNF8 | PC | 3758 |
| 19 | 376 | 41873945 | 41874354 | 409 | 0.009 | US | ENSBTAG00000048083 | KRTAP3-1 | PC | 6774 |
| 19 | 377 | 42426419 | 42427049 | 630 | 0.000 | DS | ENSBTAG00000007583 | KRT14 | PC | 3146 |
| 19 | 378 | 51052906 | 51053519 | 613 | 0.000 | DS | ENSBTAG00000045705 | | PG | 33513 |
| 19 | 379 | 51059764 | 51063463 | 3699 | 0.000 | DS | ENSBTAG00000045705 | | PG | 23569 |
| 19 | 380 | 54829885 | 54830501 | 616 | 0.044 | LR | | | NC | |
| 19 | 381 | 57555782 | 57556846 | 1064 | 0.003 | IG | ENSBTAG00000008328 | | PC | 3388 |
| 19 | 382 | 57558143 | 57559873 | 1730 | 0.010 | US | ENSBTAG00000008327 | CD300LB | PC | 7733 |
| 20 | 383 | 1657205 | 1658328 | 1123 | 0.000 | IG | ENSBTAG00000002134 | FAM196B | PC | 22909.5 |
| 20 | 383 | 1657205 | 1658328 | 1123 | 0.000 | IG | ENSBTAG00000014612 | | PC | 205390.5 |
| 20 | 384 | 2614887 | 2615794 | 907 | 0.017 | US | ENSBTAG00000024801 | RANBP17 | PC | 64780 |
| 20 | 385 | 4394840 | 4395520 | 680 | 0.004 | DS | ENSBTAG00000013863 | DUSP1 | PC | 53589 |
| 20 | 386 | 8064068 | 8064649 | 581 | 0.000 | US | ENSBTAG00000032705 | CALM2 | PC | 1692 |
| 20 | 387 | 8110357 | 8111464 | 1107 | 0.025 | DS | ENSBTAG00000042972 | U6 | snRNA | 22495 |
| 20 | 388 | 10167313 | 10168507 | 1194 | 0.000 | IG | ENSBTAG00000000561 | OCLN | PC | 33247 |
| 20 | 389 | 11244707 | 11245027 | 320 | 0.044 | DS | ENSBTAG00000010989 | PIK3R1 | PC | 84077 |
| 20 | 390 | 13872480 | 13873087 | 607 | 0.018 | IG | ENSBTAG00000016900 | TRAPPC13 | PC | 18513.5 |
| 20 | 391 | 16815022 | 16815793 | 771 | 0.029 | IG | ENSBTAG00000018616 | IPO11 | PC | 145081.5 |
| 20 | 392 | 22776119 | 22777129 | 1010 | 0.022 | DS | ENSBTAG00000043083 | U6 | snRNA | 23004 |
| 20 | 393 | 58311363 | 58312011 | 648 | 0.023 | US | ENSBTAG00000045215 | U6 | snRNA | 24700 |
| 20 | 394 | 59072435 | 59073193 | 758 | 0.013 | LR | | | NC | |
| 20 | 395 | 60021449 | 60022170 | 721 | 0.023 | LR | | | NC | |
| 20 | 396 | 63391736 | 63392369 | 633 | 0.044 | LR | | | NC | |
| 21 | 397 | 6266772 | 6267751 | 979 | 0.037 | IG | ENSBTAG00000006987 | CERS3 | PC | 5137.5 |
| 21 | 398 | 6891837 | 6893062 | 1225 | 0.026 | IG | ENSBTAG00000019823 | ADAMTS17 | PC | 378089.5 |
| 21 | 399 | 10773570 | 10774499 | 929 | 0.017 | DS | ENSBTAG00000018007 | NR2F2 | PC | 18605 |
| 21 | 400 | 20253482 | 20254461 | 979 | 0.000 | US | ENSBTAG00000001308 | | PC | 60435 |
| 21 | 401 | 25469308 | 25471129 | 1821 | 0.049 | IG | ENSBTAG00000021341 | BTBD1 | PC | 2420.5 |
| 21 | 402 | 27424396 | 27425106 | 710 | 0.000 | US | ENSBTAG00000011861 | C15orf26 | PC | 23498 |
| 21 | 403 | 36126799 | 36127666 | 867 | 0.000 | US | ENSBTAG00000048113 | bta-mir-2888-1 | miRNA | 6841 |
| 21 | 404 | 36495794 | 36498382 | 2588 | 0.003 | LR | | | NC | |
| 21 | 405 | 38574854 | 38575900 | 1046 | 0.039 | LR | | | NC | |
| 21 | 406 | 41714636 | 41715662 | 1026 | 0.029 | IG | ENSBTAG00000017565 | SCFD1 | PC | 22307 |
| 21 | 407 | 41800175 | 41801039 | 864 | 0.003 | IG | ENSBTAG00000017565 | SCFD1 | PC | 107765 |
| 21 | 408 | 46241203 | 46242270 | 1067 | 0.025 | IG | ENSBTAG00000001282 | RALGAPA1 | PC | 135012.5 |
| 21 | 409 | 55870813 | 55871955 | 1142 | 0.031 | US | ENSBTAG00000014005 | PPIP5K1 | PC | 4469 |

TABLE 2-continued

Description of each differentially methylated region (DMR) including chromosome (Chr), location, length, FDR p-value, type relative to nearest feature (Long range (LR); Downstreatm of gene (DS); Intragenic (IG); Upstream of gene (US)), Gene ID of nearest feature, feature name, feature type (non-coding (NC); snRNA, protein coding (PC), rRNA, processed pseudogene (PPG); pseudogene (PG); microRNA), and distance from feature

| Chr | DMR ID | starting nucleotide | ending nucleotide | DMR Length | FDR p-value | DMR type relative to nearest feature | Ensembl Gene ID of nearest feature | Feature Name | Feature type | DMR Distance from feature |
|---|---|---|---|---|---|---|---|---|---|---|
| 21 | 410 | 62530168 | 62531552 | 1384 | 0.026 | LR | | | NC | |
| 21 | 411 | 64874657 | 64876603 | 1946 | 0.041 | LR | | | NC | |
| 21 | 412 | 65759921 | 65760787 | 866 | 0.040 | DS | ENSBTAG00000018019 | BCL11B | PC | 81210 |
| 22 | 413 | 2609865 | 2610632 | 767 | 0.033 | US | ENSBTAG00000035286 | CMC1 | PC | 74488 |
| 22 | 414 | 6617479 | 6618665 | 1186 | 0.015 | US | ENSBTAG00000009826 | GPD1L | PC | 48116 |
| 22 | 415 | 11269338 | 11270243 | 905 | 0.030 | IG | ENSBTAG00000016566 | ITGA9 | PC | 323458.5 |
| 22 | 416 | 11981961 | 11982913 | 952 | 0.000 | DS | ENSBTAG00000009155 | SCN5A | PC | 32778 |
| 22 | 417 | 19980854 | 19981770 | 916 | 0.012 | LR | | | NC | |
| 22 | 418 | 21241017 | 21241857 | 840 | 0.010 | DS | ENSBTAG00000012904 | EDEM1 | PC | 27034 |
| 22 | 419 | 36038059 | 36038959 | 1214 | 0.002 | IG | ENSBTAG00000010581 | MAGI1 | PC | 32074 |
| 22 | 420 | 39473142 | 39473564 | 422 | 0.017 | IG | ENSBTAG00000021911 | PTPRG | PC | 29209 |
| 22 | 421 | 44710466 | 44711434 | 968 | 0.035 | US | ENSBTAG00000014091 | ARHGEF3 | PC | 99400 |
| 22 | 422 | 46905615 | 46906233 | 618 | 0.046 | IG | ENSBTAG00000013117 | CACNA2D3 | PC | 16854 |
| 22 | 423 | 47594396 | 47595317 | 921 | 0.036 | IG | ENSBTAG00000011180 | ACTR8 | PC | 2952.5 |
| 22 | 424 | 60873767 | 60874739 | 972 | 0.045 | DS | ENSBTAG00000009159 | PLXNA1 | PC | 38720 |
| 23 | 425 | 12843519 | 12844535 | 1016 | 0.010 | IG | ENSBTAG00000014063 | DNAH8 | PC | 293660 |
| 23 | 426 | 15737962 | 15738848 | 886 | 0.026 | US | ENSBTAG00000010106 | CCND3 | PC | 23590 |
| 23 | 427 | 17376215 | 17377291 | 1076 | 0.012 | LR | | | NC | |
| 23 | 428 | 28896304 | 28896961 | 657 | 0.022 | DS | ENSBTAG00000027245 | | PC | 6004 |
| 23 | 429 | 29528582 | 29530177 | 1595 | 0.000 | DS | ENSBTAG00000038928 | | PC | 10356 |
| 23 | 430 | 37498676 | 37499708 | 1032 | 0.015 | IG | ENSBTAG00000016519 | MBOAT1 | PC | 620 |
| 23 | 431 | 37942740 | 37943443 | 703 | 0.016 | LR | | | NC | |
| 23 | 432 | 38262445 | 38263486 | 1041 | 0.018 | LR | | | NC | |
| 23 | 433 | 43770147 | 43771958 | 1811 | 0.006 | LR | | | NC | |
| 23 | 434 | 44807180 | 44808358 | 1178 | 0.048 | US | ENSBTAG00000006287 | NEDD9 | PC | 43319 |
| 23 | 435 | 51526126 | 51526523 | 397 | 0.049 | DS | ENSBTAG00000026896 | FOXF2 | PC | 23198 |
| 24 | 436 | 2482434 | 2482920 | 486 | 0.041 | US | ENSBTAG00000021003 | GALR1 | PC | 64394 |
| 24 | 437 | 11858827 | 11859585 | 758 | 0.000 | LR | | | NC | |
| 24 | 438 | 21266234 | 21267032 | 798 | 0.006 | DS | ENSBTAG00000018954 | ELP2 | PC | 1814 |
| 24 | 439 | 25718197 | 25719500 | 1303 | 0.025 | US | ENSBTAG00000044063 | B4GALT6 | PC | 50843 |
| 24 | 440 | 26381925 | 26382981 | 1056 | 0.004 | US | ENSBTAG00000015238 | DSC3 | PC | 14011 |
| 24 | 441 | 26456343 | 26458029 | 1686 | 0.004 | LR | | | NC | |
| 24 | 442 | 26790857 | 26792337 | 1480 | 0.013 | LR | | | NC | |
| 24 | 443 | 28781396 | 28782895 | 1499 | 0.001 | US | ENSBTAG00000028575 | U1 | snRNA | 39988 |
| 24 | 444 | 42830443 | 42832010 | 1567 | 0.038 | US | ENSBTAG00000011171 | PIEZO2 | PC | 77427 |
| 25 | 445 | 12885712 | 12886423 | 711 | 0.014 | US | ENSBTAG00000032643 | | PC | 18332 |
| 25 | 446 | 15147938 | 15148991 | 1053 | 0.019 | LR | | | NC | |
| 25 | 447 | 16563159 | 16563937 | 778 | 0.017 | IG | ENSBTAG00000020735 | SMG1 | PC | 62154 |
| 25 | 448 | 17686697 | 17687444 | 747 | 0.044 | DS | ENSBTAG00000046240 | | miRNA | 42602 |
| 25 | 449 | 20614696 | 20615828 | 1132 | 0.015 | US | ENSBTAG00000018195 | | PC | 6524 |
| 25 | 450 | 31444762 | 31445602 | 840 | 0.029 | DS | ENSBTAG00000046179 | 5S_rRNA | rRNA | 20660 |
| 25 | 451 | 35934369 | 35936395 | 2026 | 0.010 | IG | ENSBTAG00000047808 | | PC | 5350 |
| 25 | 451 | 35934369 | 35936395 | 2026 | 0.010 | IG | ENSBTAG00000011818 | COL26A1 | PC | 25364 |
| 26 | 452 | 3547373 | 3548201 | 828 | 0.003 | LR | | | NC | |
| 26 | 453 | 10588177 | 10588800 | 623 | 0.017 | US | ENSBTAG00000001298 | STAMBPL1 | PC | 8773 |
| 26 | 454 | 12792120 | 12793313 | 1193 | 0.004 | US | ENSBTAG00000004964 | PCGF5 | PC | 85881 |
| 26 | 455 | 17642617 | 17643315 | 698 | 0.019 | US | ENSBTAG00000011743 | TLL2 | PC | 346 |
| 26 | 456 | 18787479 | 18788001 | 522 | 0.022 | US | ENSBTAG00000018566 | SFRP5 | PC | 103 |
| 26 | 457 | 23537661 | 23539299 | 1638 | 0.003 | IG | ENSBTAG00000021071 | TRIM8 | PC | 2349 |
| 26 | 458 | 34057580 | 34058628 | 1048 | 0.006 | LR | | | NC | |
| 26 | 459 | 35239718 | 35240706 | 988 | 0.035 | IG | ENSBTAG00000004899 | ABLIM1 | PC | 145612 |
| 26 | 460 | 40862278 | 40863512 | 1234 | 0.025 | US | ENSBTAG00000032106 | PPAPDC1A | PC | 82562 |
| 26 | 461 | 44677511 | 44679724 | 2213 | 0.002 | IG | ENSBTAG00000012970 | FAM53B | PC | 15273.5 |
| 27 | 462 | 3218847 | 3219545 | 698 | 0.015 | LR | | | NC | |
| 27 | 463 | 3441449 | 3442036 | 587 | 0.002 | US | ENSBTAG00000035021 | | PPG | 80747 |
| 27 | 464 | 7877879 | 7879172 | 1293 | 0.013 | LR | | | NC | |
| 27 | 465 | 15604232 | 15605489 | 1257 | 0.012 | US | ENSBTAG00000020657 | FAT1 | PC | 217 |
| 27 | 466 | 16067995 | 16069309 | 1314 | 0.048 | LR | | | NC | |
| 27 | 467 | 17959372 | 17961116 | 1744 | 0.045 | DS | ENSBTAG00000044896 | SNORA81 | snoRNA | 44066 |
| 27 | 468 | 21679991 | 21681106 | 1115 | 0.032 | US | ENSBTAG00000043920 | 5S_rRNA | rRNA | 69097 |
| 27 | 469 | 25251587 | 25252376 | 789 | 0.014 | LR | | | NC | |
| 27 | 470 | 26502257 | 26502784 | 527 | 0.019 | LR | | | NC | |
| 27 | 471 | 27521640 | 27522652 | 1012 | 0.044 | LR | | | NC | |
| 27 | 472 | 27722327 | 27723424 | 1097 | 0.039 | LR | ENSBTAG00000004150 | NRG1 | PC | 98810.5 |
| 27 | 473 | 30641856 | 30643184 | 1328 | 0.011 | IG | ENSBTAG00000010241 | UNC5D | PC | 220943 |
| 27 | 474 | 38816973 | 38818019 | 1046 | 0.000 | DS | ENSBTAG00000016473 | | PC | 44121 |
| 27 | 475 | 39484958 | 39486523 | 1565 | 0.004 | LR | | | NC | |
| 27 | 476 | 42576104 | 42577069 | 965 | 0.013 | LR | | | NC | |
| 28 | 477 | 4967052 | 4967928 | 876 | 0.040 | LR | | | NC | |

TABLE 2-continued

Description of each differentially methylated region (DMR) including chromosome (Chr), location, length, FDR p-value, type relative to nearest feature (Long range (LR); Downstreatm of gene (DS); Intragenic (IG); Upstream of gene (US)), Gene ID of nearest feature, feature name, feature type (non-coding (NC); snRNA, protein coding (PC), rRNA, processed pseudogene (PPG); pseudogene (PG); microRNA), and distance from feature

| Chr | DMR ID | starting nucleotide | ending nucleotide | DMR Length | FDR p-value | DMR type relative to nearest feature | Ensembl Gene ID of nearest feature | Feature Name | Feature type | DMR Distance from feature |
|---|---|---|---|---|---|---|---|---|---|---|
| 28 | 478 | 5129438 | 5130456 | 1018 | 0.008 | LR | | | NC | |
| 28 | 479 | 8657799 | 8658504 | 705 | 0.035 | US | ENSBTAG00000042807 | U6 | snRNA | 6303 |
| 28 | 480 | 12445009 | 12446777 | 1768 | 0.026 | LR | | | NC | |
| 28 | 481 | 20805898 | 20807277 | 1379 | 0.044 | LR | | | NC | |
| 28 | 482 | 26107229 | 26107776 | 547 | 0.046 | US | ENSBTAG00000006431 | NEUROG3 | PC | 43454 |
| 28 | 483 | 27143350 | 27144524 | 1174 | 0.019 | IG | ENSBTAG00000009984 | SGPL1 | PC | 10511 |
| 28 | 484 | 42131338 | 42132010 | 672 | 0.041 | US | ENSBTAG00000046597 | GPRIN2 | PC | 6328 |
| 28 | 485 | 44961004 | 44962038 | 1034 | 0.025 | IG | ENSBTAG00000002669 | RASSF4 | PC | 52722 |
| 28 | 486 | 46266697 | 46267364 | 667 | 0.001 | US | ENSBTAG00000045503 | 5S_rRNA | rRNA | 143 |
| 29 | 487 | 1039718 | 1040841 | 1123 | 0.002 | IG | ENSBTAG00000003550 | C11orf54 | PC | 16184.5 |
| 29 | 488 | 1896777 | 1897216 | 439 | 0.035 | US | ENSBTAG00000047614 | | PC | 14023 |
| 29 | 489 | 1987284 | 1987993 | 709 | 0.048 | IG | ENSBTAG00000004081 | FAT3 | PC | 617486.5 |
| 29 | 490 | 2280779 | 2281886 | 1107 | 0.031 | IG | ENSBTAG00000004081 | FAT3 | PC | 323792.5 |
| 29 | 491 | 12843912 | 12845727 | 1815 | 0.044 | IG | ENSBTAG00000033731 | PRCP | PC | 24689.5 |
| 29 | 492 | 16741688 | 16742601 | 913 | 0.048 | LR | | | NC | |
| 29 | 493 | 21147230 | 21148172 | 942 | 0.019 | LR | | | NC | |
| 29 | 494 | 23779535 | 23780087 | 552 | 0.008 | LR | | | NC | |
| 29 | 495 | 24278160 | 24278608 | 448 | 0.025 | DS | ENSBTAG00000045401 | U1 | snRNA | 93208 |
| 29 | 496 | 28203153 | 28203747 | 594 | 0.017 | DS | ENSBTAG00000047716 | | PC | 3750 |
| 29 | 497 | 36017739 | 36018620 | 881 | 0.014 | DS | ENSBTAG00000042807 | U7 | snRNA | 169125.8353 |
| 29 | 498 | 47373613 | 47374227 | 614 | 0.032 | LR | | | NC | |
| X | 499 | 99287745 | 99288353 | 608 | 0.025 | LR | | | NC | |
| X | 500 | 146990489 | 146992084 | 1595 | 0.000 | LR | | | NC | |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of selecting a cow having a high milk-yielding phenotype, the method comprising:
   a. determining the level of methylation in the DMR379 differentially methylated genomic region in a leukocyte sample obtained from a subject cow;
   b. comparing the determined level of methylation to a level of methylation of the DMR379 differentially methylated genomic region obtained from a control cow that has a low milk yield phenotype;
   c. determining that the level of methylation as determined in step a. is higher than the level of methylation of the DMR379 differentially methylated genomic region obtained from the control cattle that has low milk yield phenotype;
   d. selecting the subject cow as having a high milk yield phenotype; and
   e. obtaining milk from the subject cow selected as having a high milk yield phenotype.

* * * * *